(12) United States Patent
Kawahara et al.

(10) Patent No.: US 6,337,897 B1
(45) Date of Patent: Jan. 8, 2002

(54) FLUORESCENT X-RAY ANALYZER

(75) Inventors: Naoki Kawahara; Kouichi Aoyagi, both of Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 09/421,242

(22) Filed: Oct. 20, 1999

(30) Foreign Application Priority Data

Oct. 30, 1998 (JP) .......................................... 10-310056
Aug. 23, 1999 (JP) .......................................... 11-235468

(51) Int. Cl.$^7$ .......................................... G01N 23/223
(52) U.S. Cl. .......................................... 378/45; 378/148
(58) Field of Search .......................................... 378/45–50, 148

(56) References Cited

U.S. PATENT DOCUMENTS 5,408,512 A * 4/1995 Kuwabara et al. ............. 378/45
5,684,857 A * 11/1997 De Bokx ..................... 378/45

OTHER PUBLICATIONS

Patent Abstracts of Japan, Publication No. 05126998 A, May 25, 1993, Shoji.

* cited by examiner

*Primary Examiner*—Craig E. Church
(74) *Attorney, Agent, or Firm*—Sughrue Mion, PLLC

(57) ABSTRACT

A fluorescent X-ray analyzer includes a detector (6) for detecting fluorescent X-rays (5) emitted from a sample piece (1) to be analyzed, and a first collimator (10) disposed between the sample piece (1) and the detector (6) supported for movement between inserted and retracted positions with respect to a path of travel of the fluorescent X-rays (5) towards the detector (6). The first collimator (10) comprises a wall (11) adjacent the sample piece (1) that is stepped to provide stepped wall segments (11a, 11b, 11c) having respective apertures (12a, 12b, 12c) of varying diameters defined therein. The smaller the aperture, the closer it is to the sample piece (1) when one of the apertures (12a, 12b, 12c) is selected according to a size of a target area of the sample piece (1) to be measured and is then brought in register with the path of travel of the fluorescent X-rays (5) towards the detector (6).

16 Claims, 17 Drawing Sheets

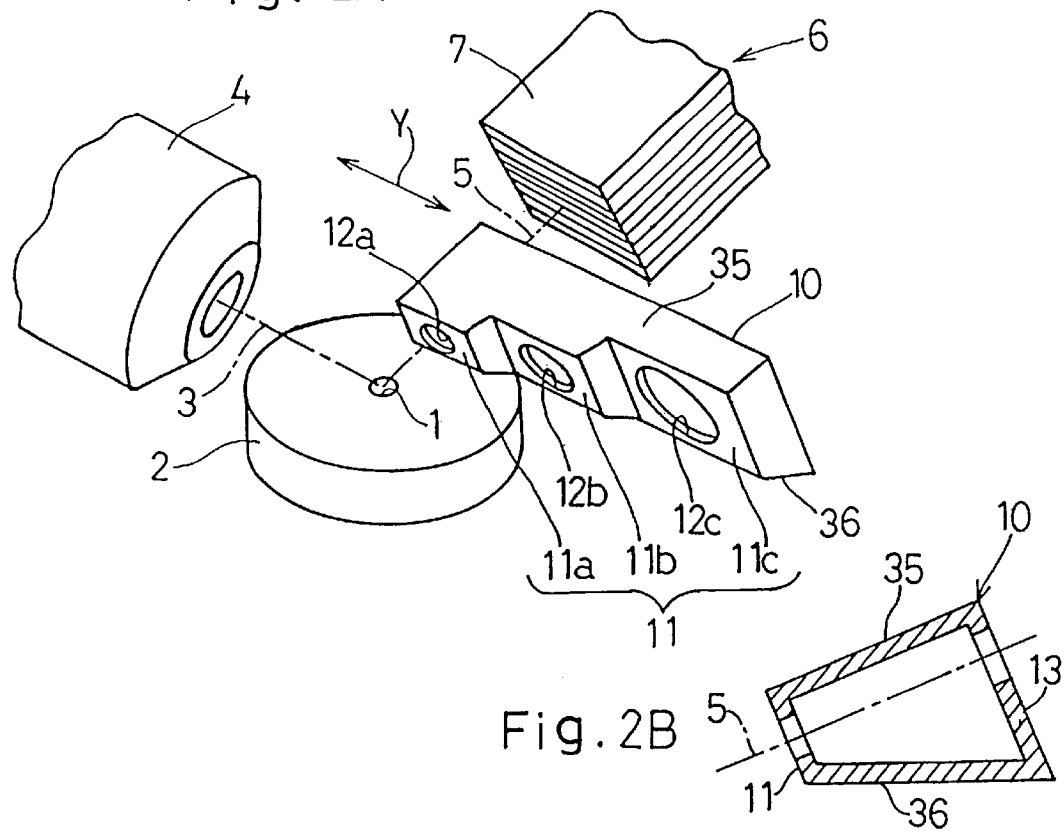
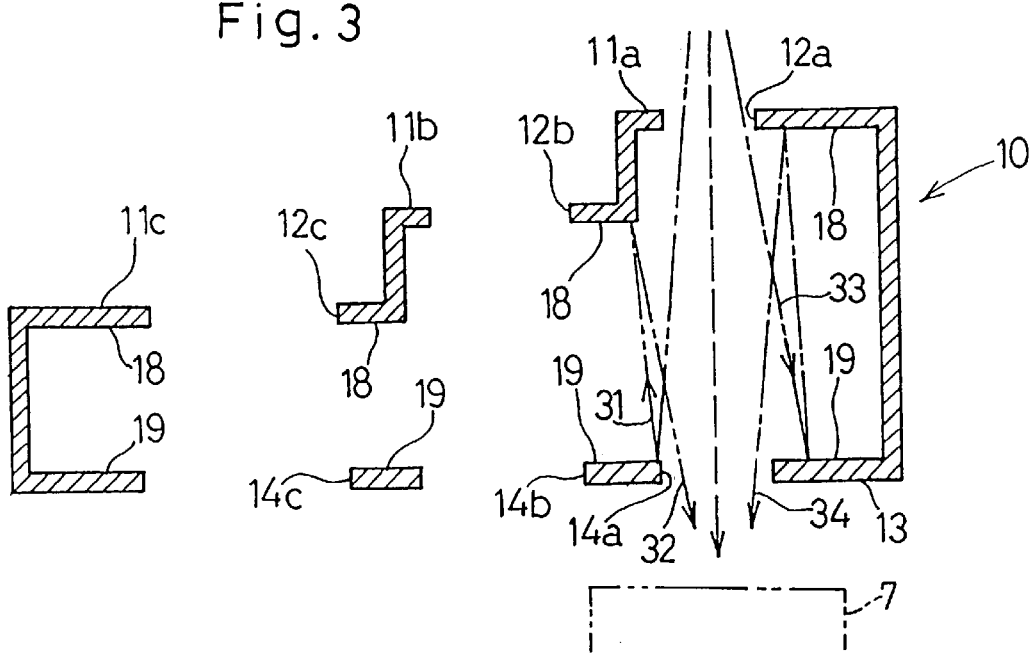

FLUORESCENT X-RAY ANALYZER

BACKGROUND OF THE INVENTION

1. Field of the Invention

The present invention generally relates to a fluorescent X-ray analyzer and, more particularly, to the fluorescent X-ray analyzer of a type provided with a collimator for restricting the field of view so that fluorescent X-rays and/or scattering X-rays generated from sources other than a sample piece being analyzed will not reach a detecting means.

2. Description of the Prior Art

Generally in a fluorescent X-ray analyzer utilizing parallel beams, as shown in FIG. 19, a sample piece 1 fixedly supported on a sample table is generally radiated with primary X-rays 3 generated from an X-ray tube 4 to excite the sample piece 1. The sample piece 1 so excited generates fluorescent X-rays 5 which are subsequently guided through a collimator 10A to a solar slit 7 to extract the fluorescent X-rays 5 in the form of parallel beams. The fluorescent X-rays 5 emerging from the solar slit 7 are subsequently monochromatized by a monochromator 8 according to spectrum of different wavelengths corresponding to elements contained in the sample piece 1 with a detector 9 consequently detecting the monochromatized X-rays.

The collimator 10A disposed between the sample piece 1 and the solar slit 7 is employed for the following reason.

Since the primary X-rays 3 emanating from the X-ray tube 4 irradiate not only the sample piece 1 to be analyzed, but also the sample table 2, the absence of the collimator results in that as shown in FIG. 20A, not only the fluorescent X-rays generated from the sample piece 1, but also a large amount of disturbing rays such as fluorescent X-rays and/or scattering X-rays generated from a portion 2a of the sample table 2 adjacent and surrounding the sample piece 1 impinges upon the detector 9. For this reason, the disturbing rays eventually constitute a background with respect to the spectrum of the fluorescent X-rays emanating from the sample piece 1, accompanied by reduction in the S/N ratio.

In contrast thereto, the use of the collimator 10A results in that as shown in FIG. 20B, the field of view, or coverage, of the detector 9 is restricted to a portion 2a of the sample table 2 surrounding the sample piece 1. Specifically, this portion 2a of the sample table 2 encompassed by the collimator 10A shown in FIG. 20B, although constituting a source of the disturbing rays, is limited to an area smaller than the portion 2a covered by the detector 9 when no collimator 10A is used, and therefore, the most of the disturbing rays are intercepted by the collimator 10A and does not reach the detector 9, resulting in improvement of the S/N ratio.

The collimator 10A discussed above is of a structure including, as shown in FIG. 19, an oblong plate member having a plurality of, for example, three field-limiting apertures 12a, 12b and 12c of varying diameters defined therein in a row conforming to a direction of sliding motion of the collimator 10A shown by the arrow Y The apertures 12a to 12c are selectively brought into alignment with the path of travel of the fluorescent X-rays 5 towards the solar slit 7 one at a time depending on the size of a target area of the sample piece 1 to be measured.

However, as shown in FIG. 20B, there is a certain distance L between the collimator 10A and the sample piece 1. Accordingly, even though one of the apertures, for example, the aperture 12a of a diameter substantially equal to the size of the sample piece 1 is selected, the "eye" of the detector 9 looking at the sample piece 1 through the selected aperture 12a is such that even the disturbing rays emanating from that portion 2a closely exteriorly surrounding the sample piece 1 are apt to pass through the selected aperture 12a and then to be incident upon the detector 9, eventually resulting in incapability of improving the S/N ratio.

If in an attempt to prevent the disturbing rays from entering the detector, one of the apertures which is of a diameter smaller than the size of the sample piece 1 is selected, the intensity of the fluorescent X-rays passing through the selected aperture will decrease, resulting in reduction in sensitivity of detection.

In order to alleviate the above discussed problems, the Japanese Patent No. 2,674,675 discloses the use of such a collimator 10B as shown in FIG. 21. The suggested collimator 10B comprises a plurality of, for example, three tubes 15a to 15c having varying inner diameters each corresponding to the size of a target area of the sample piece 1 to be measured and, also, varying lengths with the largest length chosen for the smallest inner diameter of the tube and the smallest length chosen for the largest inner diameter of the tube such that when one of the tubes 15a to 15c is selected, the smaller the inner diameter of the tube, the closer the tube is to the sample piece 1. In such case, if one of the tubes 15a to 15c in the collimator 10B is properly selected according to the particular size of the sample piece 1 to be analyzed, the "eye" of the detector 9 looking at the sample piece 1 through the selected tube is such as to encompass only the sample piece 1 and, therefore, the disturbing rays emanating from an area other than the sample piece 1 can be effectively intercepted. Therefore, with no need to reduce the diameter of the corresponding aperture down to a value smaller than the size of the sample piece 1, any possible entry of the disturbing rays emanating from the area other than the sample piece 1 to the detector through the solar slit 7 can be effectively minimized, accompanied by improvement in S/N ratio without the sensitivity of detection being decreased. However, the use of the collimator 10B has been found having such a problem that as shown in FIG. 22, when the fluorescent X-rays 5 emanating from the sample piece 1 are partially cut off by, for example, the tube 15a, a portion 5a of the fluorescent X-rays 5 emanating from the sample piece 1 tend to impinge upon an inner wall surface 16a of the tube 15a, resulting in generation of disturbing rays 30, such as fluorescent X-rays and/or scattering X-rays, from the inner wall surface 16a which will eventually enter the detector through the solar slit 7. Accordingly, the S/N ratio cannot yet be improved sufficiently. Also, respective longitudinal axes of those tubes 15a to 15c must extend parallel to the solar slit foil and, thus, a high processing precision is required to manufacture the collimator 10B, accompanied by reduction in workability.

On the other hand, in the prior art fluorescent X-ray analyzer, as shown in FIG. 21, the sample piece 1 is irradiated by the primary X-rays 3 with the direction of an axis of the X-ray source 4 inclined relative to the sample piece 1, so that the fluorescent X-rays 5 generated from the sample piece 1 while the X-ray source 4 is positioned as close as possible to the sample piece 1 to cause the latter to receive an increased radiation intensity can enter the detector. The radiation intensity of the primary X-rays 3 towards the target area of the sample piece 1 to be measured means the total radiation intensity of the primary X-rays 3 towards the entire target area of a sample surface 1a to be measured. As a result of the simulated test conducted to determine a pattern of distribution of radiation intensity of the primary X-rays 3 over an imaginary irradiation plane including the sample surface 1a and its plane extension, inclination of the direction of the axis of the X-ray source 4 has resulted in that as shown by a curve B in FIG. 23, distribution of the radiation intensity was not maximized at a location C where the radiation center axis of the X-ray source 4 extends to the imaginary irradiation plane, but was maximized at a location M displaced in a direction conforming to the direction of inclination of the X-ray source 4, thus representing an asymmetric pattern of distribution of the radiation intensity.

Accordingly, assuming, for example, that the target area of the sample piece 1 to be measured has a relatively large diameter D3, the radiation intensity (corresponding to the hatched surface area) of the primary X-rays 3 projected onto the target area of the sample piece 1 to be measured will be maximized at a location shown by D3 whereas if the target area of the sample piece 1 to be measured has a relatively small diameter D1, the radiation intensity thereof will be maximized at a location shown by D1. Thus, depending on the size of the target area of the sample piece 1, the location at which the radiation intensity is maximized varies. Accordingly, the inventor of the present invention have suggested in the Japanese Patent Application No. 8-312673 (U.S. patent application Ser. No. 09/127,724), the use of a movable sample table 2 that can be moved to an optimum position at which the radiation intensity of the primary X-rays 3 towards the target area of the sample piece 1 can be maximized to thereby maximize the efficiency of utilization of the primary X-rays 3 from the X-ray source 4.

However, any of the prior art collimators 10A and 10B discussed hereinabove is so designed that the location C where the radiation center axis of the X-ray source 4 extends to the imaginary irradiation plane may be chosen as a location where the collimators 10A and 10B work to partially cut off the fluorescent X-rays 5. In other words, even though any of the apertures in the respective collimators 10A and 10B is chosen, the center at which the aperture encompasses necessarily lies at a certain location C. On the other hand, as discussed above, if the target area of the sample piece 1 to be measured is moved to the optimum position, the position M at which the intensity of X-ray radiation is maximized is displaced from the location C and, therefore, if the center at which the aperture encompasses lies at the location C, the fluorescent X-rays 5 emanating from the target area to be measured will not be sufficiently impinge upon the detector, consequently, the S/N ratio will not be sufficiently improved.

SUMMARY OF THE INVENTION

Accordingly, the present invention is intended to provide an improved fluorescent X-ray analyzer equipped with a collimator which is effective to improve the S/N ratio as compared with that exhibited by the prior art collimator, without accompanying any possible reduction in sensitivity of detection and which is excellent in workability.

In order to accomplish the above described object of the present invention, one aspect thereof provides a fluorescent X-ray analyzer which comprises a detecting means for detecting fluorescent X-rays emitted from a sample piece to be analyzed, and a first collimator disposed between the sample piece and the detecting means and supported for movement between inserted and retracted positions with respect to a path of travel of the fluorescent X-rays towards the detecting means. The first collimator comprises a wall adjacent the sample piece that is stepped to provide stepped wall segments having respective apertures of varying diameters defined therein. The smaller the aperture, the closer it is to the sample piece when one of the apertures is selected according to a size of a target area of the sample piece to be measured and is then brought in register with the path of travel of the fluorescent X-rays towards the detecting means.

According to the construction described above, by suitably selecting one of the aperture according to the size of the target area of the sample piece to be measured, since only the sample piece can be encompassed when the sample piece is viewed from the side of the detecting means, as is the case with the collimator described in connection with the prior art, any possible entry of the disturbing rays, generated from other than the sample piece, into the detecting means can be prevented and, therefore, the S/N ratio can be improved without the detection sensitivity being lowered. Also, since the path of travel of the fluorescent X-rays passing through any of the apertures is not of a type having a narrow width surrounded by an inner wall surface, the disturbing rays will hardly occur from the inner wall surface and, hence, the S/N ratio can further be improved as compared with the prior art.

Preferably, the first collimator comprises a substrate and a projection formed on the substrate, said projection having a tip where the stepped wall segments are formed.

Also preferably, a second collimator is disposed between the first collimator and the detecting means and supported for movement between inserted and retracted positions with respect to the path of travel of the fluorescent X-rays towards the detecting means. This second collimator has one or more apertures of a diameter larger than that of any one of the apertures in the first collimator. According to this structure, since one or more apertures of the diameter larger than that of any one of the apertures in the first collimator, which are not required to be approached towards the target area of the sample piece to be measured are defined in the second collimator which is a member separate from the first collimator and since the second collimator is positioned rearwards of the first collimator, as compared with all of the apertures are arranged in the first collimator, the length in a lateral direction can be reduced, making it possible to render the collimator in a compact size.

Again preferably, a drive mechanism is provided for moving the sample piece to an optimum position at which a radiation intensity of a primary X-rays towards a target area of the sample piece to be measured can be maximized depending on the size of the target area of the sample piece. In such case, the apertures in the first and second collimators are arranged so as to encompass the target area of the sample piece as viewed from the detecting means. According to this structure, since the apertures in the first and second collimators are so arranged as to encompass the target area to be measured then held at the optimum position at which the radiation intensity of the primary X-rays is maximum, the fluorescent X-rays generated from the sample piece can be sufficiently utilized to further improve the S/N ratio.

An another aspect of the present invention provides a fluorescent X-ray analyzer which comprises a detecting means for detecting fluorescent X-rays emitted from a sample piece to be analyzed, and a first collimator disposed between the sample piece and the detecting means. The first collimator has a plurality of apertures defined therein, and also has a flat wall adjacent the sample piece, at least a portion of said flat wall being positioned within an area of irradiation of primary X-rays generated from a X-ray source, and a shielding wall for preventing the primary X-rays, generated by the X-ray source, from entering a path of travel of the fluorescent X-rays from the side of the detecting means of the wall adjacent the sample piece.

According to this construction, since the wall adjacent the sample piece is flat, it can easily be processed. Also, since the provision has been made of the shielding wall for preventing the primary X-rays, which would serve as disturbing rays, from entering the path of travel of the fluorescent X-rays, the disturbing rays can be prevented with the S/N ratio improved consequently.

A further another aspect of the present invention provides a fluorescent X-ray analyzer which comprises a detecting means for detecting fluorescent X-rays emitted from a sample piece to be analyzed, and a first collimator disposed between the sample piece and the detecting means. The first collimator comprises a flat wall adjacent the sample piece and having a plurality of apertures defined therein, and a shielding portion provided at a front side of said flat wall for preventing primary X-rays, generated by a X-ray source, from entering any one of the apertures.

According to this construction, since the shielding portion serves to prevent the primary X-rays, which would constitute disturbing rays, from entering any one of the apertures, the S/N ratio can be improved.

Preferably, the sample piece is supported by a sample table and the first collimator is arranged so as to receive fluorescent X-rays in a direction inclined relative to the sample table. The first collimator has a corner area confronting the sample table, which is cutout to define a cutout surface parallel to a surface of the sample table. According to this structure, any of the apertures in the first collimator can be brought close to the sample table without being interfered with the sample table accompanied by improvement of the S/N ratio.

Also preferably, the shielding portion may be either a visor formed integrally with the first collimator or a visor formed by fitting a separate plate to the first collimator. Further preferably, the visor of the first collimator has an extension which is formed with a primary X-ray aperture. According to this structure, since the primary X-rays partially cut off by the primary X-ray aperture impinges upon the sample piece, any possible generation of the fluorescent X-rays from around the sample piece can advantageously prevented, resulting in increase of the measurement accuracy.

Furthermore, the shielding portion is preferably arranged to incline in a direction in which a portion of the wall adjacent the sample piece close towards the X-ray source approaches a center axis of the X-ray source.

A still further aspect of the present invention provides a fluorescent X-ray analyzer which comprises a detecting means for detecting flourescent X-rays emitted from a sample piece to be analyzed, and a first collimator comprises a plate member having a plurality of apertures defined therein and supported for movement between inserted and retracted position with respect to a path of travel of fluorescent X-rays. A second collimator is disposed between the first collimator and the detecting means and comprises a plate member having an aperture defined therein of a diameter larger than that of the apertures in the first collimator. The second collimator is supported for movement between inserted and retracted position with respect to the path of travel of the fluorescent X-rays.

According to this construction, as compared with the case in which all of the apertures of all diameters are arranged in the first collimator, the length of the collimator in a lateral direction can be shortened and, consequently, the collimator can be compactized. Also, since the first and second collimators are employed in the form of a flat plate member, the processing is easy to achieve. In addition, the smaller the target area to be measured, the more does the S/N ratio require to be improved, but this can be implemented by positioning the first collimator having the aperture of a relatively small diameter closer to the sample piece than the second collimator.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a schematic perspective view of an important portion of the fluorescent X-ray analyzer shown in FIG. 1;

FIG. 2B is a schematic longitudinal sectional view of a first collimator employed in the fluorescent X-ray analyzer shown in FIG. 1;

FIG. 3 is a schematic transverse sectional view of the first collimator employed in the fluorescent X-ray analyzer shown in FIG. 1;

DESCRIPTION OF THE EMBODIMENTS

Figure 1:
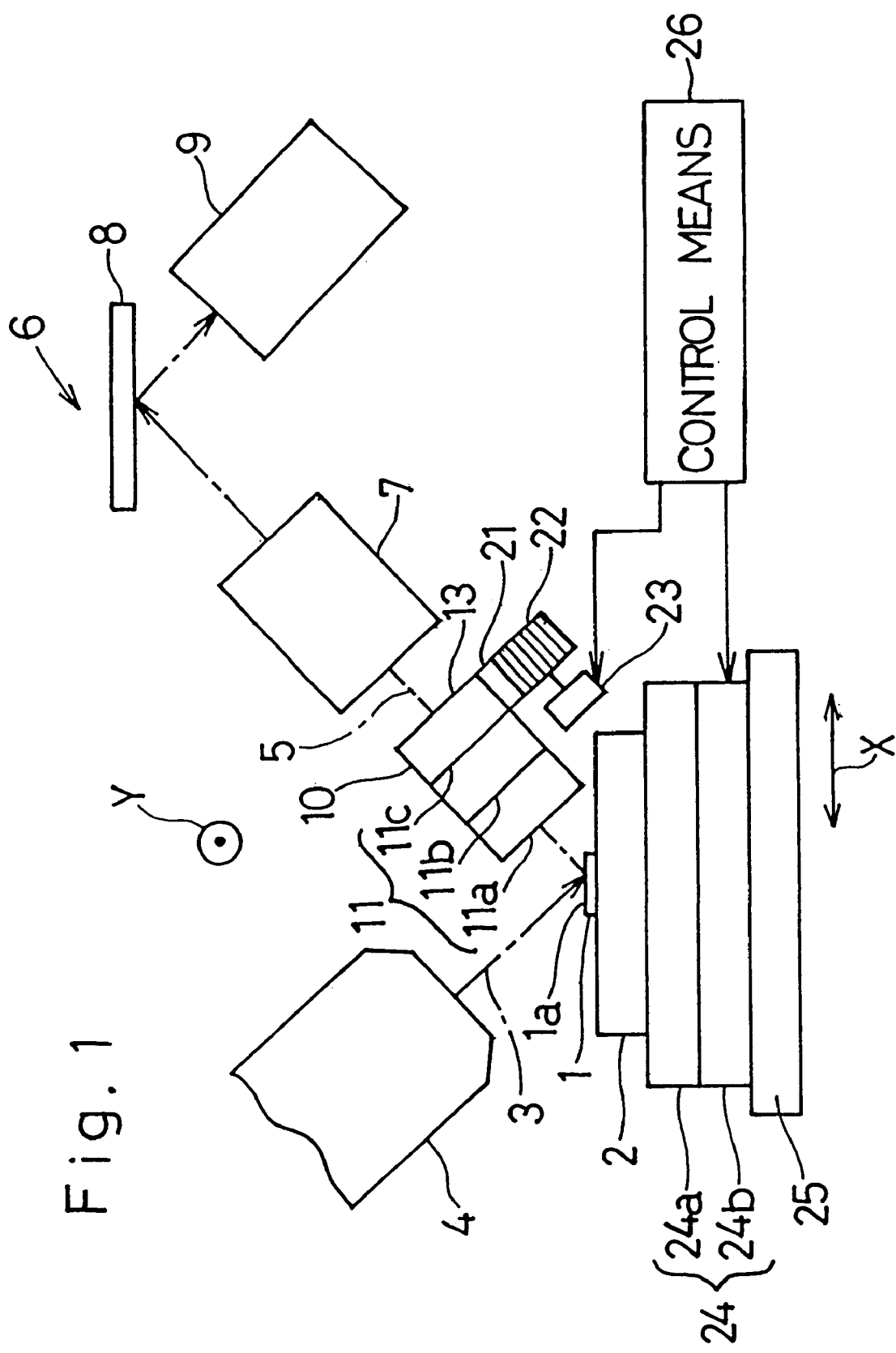
FIG. 1 is a schematic side view of a fluorescent X-ray analyzer according to a first preferred embodiment of the present invention.

A fluorescent X-ray analyzer according to a first preferred embodiment of the present invention will first be described with reference to FIGS. 1 to 4. Referring particularly to FIG. 1, the fluorescent X-ray analyzer shown therein comprises a sample table 2 for the support thereon of a sample piece 1, an X-ray source 4 for projecting primary X-rays 3 towards a surface 1a of the sample piece 1 at an inclined angle, and a detecting means 6 for measuring the intensity of fluorescent X-rays 5 which are a kind of secondary X-rays generated from the sample piece 1. The detecting means 6 includes a solar slit 7 for rendering the fluorescent X-rays 5 to be parallel, a monochromator 8, a detector 9 and a goniometer (not shown). It is to be noted that the detecting means 6 need not necessarily be of a parallel beam method in which parallel beams can be drawn through the solar slit 7, but may be a so-called focusing method. In such case, a curvature crystal is employed for a monochromator and the detector is positioned at a point of focus, with no solar slit 7 for paralleling employed.

A first collimator 10 is disposed on a path of travel of the fluorescent X-rays 5 from the sample piece 1 towards the detecting means 6. As shown in FIG. 2B, the first collimator 10 includes a front wall 11 adjacent the sample piece 1, a rear wall 13 adjacent the detecting means 6, and top and bottom walls 35 and 36, all assembled together to render the first collimator 10 to represent a generally trapezoidal shape in its longitudinal section. It is to be noted that the first collimator 10 may be fabricated either by bending a plate member or by grinding a thick plate or a block. As shown in FIG. 2A, the front wall 11 facing towards the sample piece 1 is stepped in a ladder fashion to have a plurality of, for example, first, second and third front wall segments 11a, 11b and 11c each having a first, second or third aperture 12a, 12b or 12c of a varying diameter defined therein. The closer does the front wall segment of the front wall 11 protrude towards the sample piece 1, the smaller the diameter of the corresponding aperture is. In the illustrated embodiment, the first front wall segment 11a is closest of all to the sample piece 1 and, hence, the aperture 12a defined in the first front wall segment 11a is the smallest of all. Accordingly, it will readily be seen that when the first collimator 10 is moved to bring into alignment with the path of travel of the fluorescent X-rays 5 one of the first to third apertures 12a to 12c that is selected to suit to the size of a target area of the sample piece 1 to be measured, the aperture of the smallest diameter approaches is spaced the smallest available distance from the sample piece 1. In this way, with no need to further reduce the diameter of the first to third apertures 12a to 12c, any possible passage of X-rays, emanating from an area other than the target area, through the selected aperture can advantageously be suppressed.

Thus by properly selecting one of the first to third apertures 12a to 12c according to the size of the target area of the sample piece 1, the "eye" of the detecting means 6 looking at the sample piece 1 through the selected aperture 12a, 12b or 12c is such as to encompass only the sample piece 1 and, therefore, disturbing rays emanating from an area other than the sample piece 1 can be effectively intercepted, resulting in improvement of the S/N ratio without accompanying any possible reduction in sensitivity of detection.

Also, since the first collimator 10 is prepared from the plate member with the first to third apertures 12a to 12c defined therein, the first collimator 10 has an excellent workability.

As best shown in FIG. 3, the rear wall 13 facing towards the solar slit 7 of the first collimator 10 is in the form of a flat plate having first to third auxiliary apertures 14a, 14b and 14c defined therein in alignment with the first to third apertures 12a to 12c, respectively. The first to third auxiliary apertures 14a to 14c may have a diameter equal to or larger than that of the corresponding aperture 12a, 12b or 12c and are so arranged as to allow the "eye" of the detecting means 6 to look at only the sample piece 1. It is to be noted that the first collimator 10 may not have the rear wall 13 facing towards the solar slit 7, but may suffice to have only the front wall 11 having the first to third apertures 12a to 12c defined therein for partially cutting off the fluorescent X-rays 5.

As shown in FIG. 1, the first collimator 10 of the fluorescent X-ray analyzer also is movably mounted on a guide member (not shown) extending in a direction Y perpendicular to the plane of the sheet of the drawing. A rack 21 is secured to a bottom area of the first collimator 10 and is drivingly meshed with a pinion 22 rigidly mounted on a drive shaft of a stepping motor 23. Accordingly, the first collimator 10 can be slid along the guide member (not shown) in the direction Y by the drive of the stepping motor 23.

The fluorescent X-ray analyzer also comprises a drive mechanism 24 such as an X-Y stage for moving the sample piece 1 to an optimum position at which the radiation intensity of the primary X-rays 3 irradiating the target area to be measured can attain a maximum value according to the size of the target area of the sample piece 1. The sample table 2 is therefore fixedly mounted on a top portion 24a of the drive mechanism 24. The top portion 24a of the X-Y stage is mounted on a lower portion 24b for movement in a direction shown by X whereas the lower portion 24b of the X-Y stage is mounted on a base 25 for movement in a direction Y perpendicular to the direction X. In other words, the X-Y represents the orthogonal coordinates set on the imaginary irradiating surface. It is to be noted that the drive mechanism 24 may be a r-θ stage, in which case the r-θ represents the polar coordinates set on the imaginary irradiation plane with its pole taken at the point of center of the sample surface 1a.

The X-Y stage 24 and the first collimator 10 are controlled by a control means 26. In other words, the control means 26 controls the X-Y stage 24 so that the sample table 2 can be moved to the optimum position at which the radiation intensity of the primary X-rays 3 towards the target area of the sample piece 1 can be maximized, according to the size of the target area of the sample piece 1 and, also, controls the stepping motor 23 for driving the first collimator 10 to select one of the first to third apertures 12a to 12c in the first collimator 10 according to the size of the target area of the sample piece 1 to be measured, so that only the fluorescent X-rays 5 emanating from the target area of the sample piece 1 to be measured can be received by the detecting means 6 through the selected aperture 12a, 12b or 12c.

Figure 4:
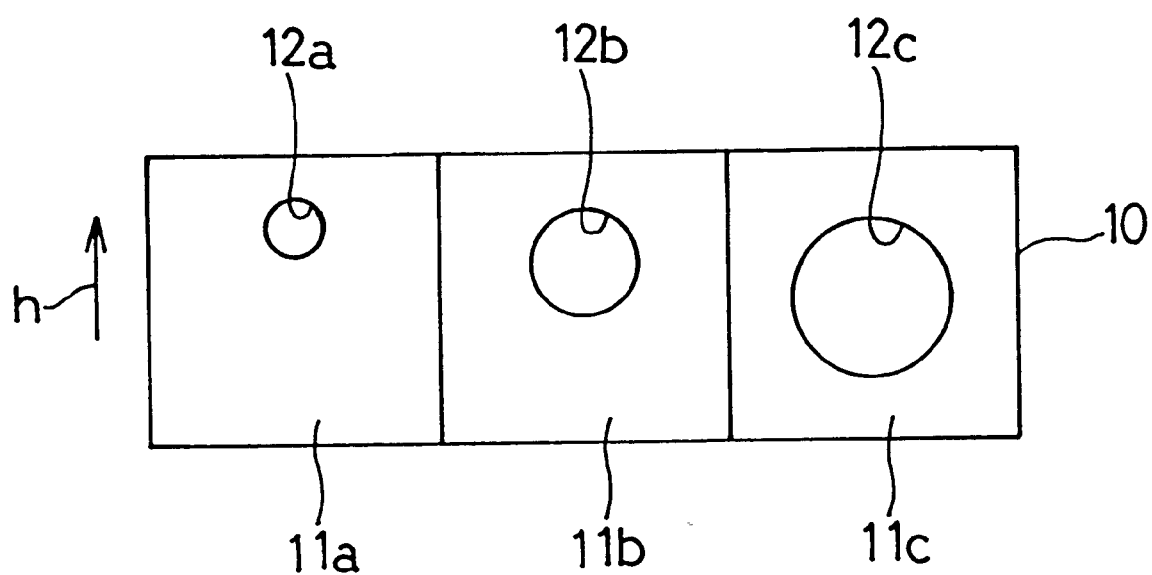
FIG. 4 is a schematic front elevational view of the first collimator employed in the fluorescent X-ray analyzer shown in FIG. 1.

Thus, since the position of the sample piece 1 can be moved according to the size of the target area of the sample piece 1, as shown in FIG. 4, respective positions of centers of the first to third apertures 12a to 12c in the first collimator 10 do not lie at the same level with respect to the heightwise direction h of the first collimator 10, but are progressively displaced in the heightwise direction h. This is for the purpose that, when viewing from the detecting means 6, the target area of the sample piece 1 located at the optimum position (FIG. 23) at which the radiation intensity of the primary X-rays 3 towards the target area of the sample piece 1 attains the maximum value can be encompassed, and by so arranging the first to third apertures 12a to 12c in the manner described above, the fluorescent X-rays emanating from the target area of the sample piece 1 to be measured can be sufficiently passed onto the detecting means 6 to thereby further improve the S/N ratio.

Figure 23:
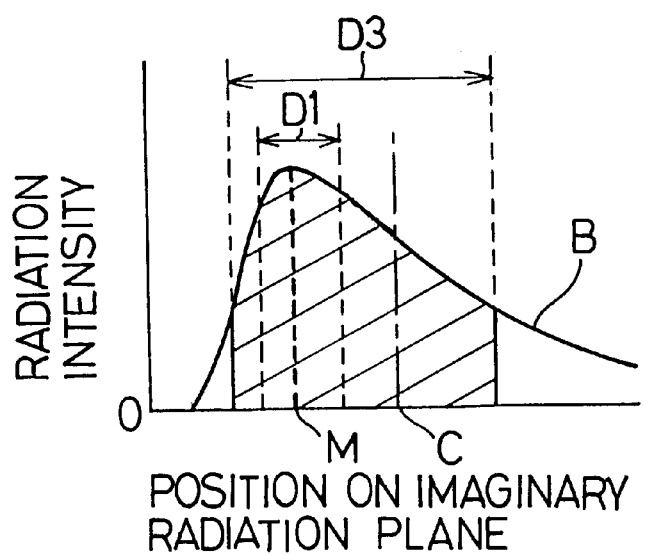
FIG. 23 is a graph showing a pattern of distribution of radiation intensities of the primary X-rays on the imaginary irradiation plane that is exhibited when the primary X-rays are irradiated in an inclined fashion.

The pattern of distribution B of the radiation intensities of the primary X-rays 3 on the imaginary irradiation plane can be determined beforehand by means of a simulated calculation or a series of experiments as shown in FIG. 23. In this pattern of distribution B of the radiation intensities, it is also similarly determined that if the target area of the sample piece 1 to be measured is of a size having a diameter D3, the radiation intensity of the primary X-rays 3 towards the target area of the sample piece 1 to be measured is maximized within the hatched area shown in the graph of FIG. 23. Accordingly, the position on the imaginary irradiation plane corresponding to the hatched area in the graph of FIG. 23 is stored in the control means 26 as the position corresponding to the diameter D3 of the target area. Similarly, the respective positions associated with the diameters D1 and D2 (wherein D1<D2<D3) are stored in the control means 26.

On the other hand, once the size of the target area of the sample piece 1 is determined, the diameter of the aperture in the first collimator 10 and the distance between the aperture in the first collimator 10 and the target area to be measured, both required to permit only the fluorescent X-rays emanating from the target area to be measured to enter the detecting means 6. Based on this, if the target area to be measured has one of, for example, three different sizes, the fact that the apertures in the first collimator 10 which correspond respectively to the diameters D1, D2 and D3 of the target area to be measured are those identified by 12a, 12b and 12c, respectively, is stored in the control means 26.

The operation of the fluorescent X-ray analyzer designed according to the first preferred embodiment of the present invention will now be described.

At the outset, as shown in FIG. 1, the sample piece 1 is fixedly placed on the sample table 2 with its center aligned with the center of the sample table 2. When information describing that the target area to be measured has a diameter identified by, for example, D1 is inputted to the control means 26, the control means 26 controls the X-Y stage 24 so that the sample table 2 can be moved to the position corresponding to the diameter D1 of the target area to be measured which has been stored in the control means 26, that is, the position at which the radiation intensity of the primary X-rays 3 towards the target area of the sample piece 1 to be measured attains the maximum value. Simultaneously therewith, the control means 26 controls the stepping motor 23 so that the first aperture 12a in the first collimator 10 corresponding to the diameter D1 of the target area to be measured which has been stored in the control means 26 can be selected, that is, only the fluorescent X-rays 5 emanating from the target area can enter the detecting means 6. As a result of rotation of the stepping motor 23, the first collimator 10 is moved in the direction Y shown in FIG. 2A to bring the first aperture 12a in the first collimator 10 in alignment with the path of travel of the fluorescent X-rays 5 between the sample piece 1 and the detecting means 6.

Starting from this condition, when the sample piece 1 generates the fluorescent X-rays 5 as a result of irradiation of the primary X-rays 3 from the X-ray source 4, the fluorescent X-rays 5 pass through the first aperture 12a. At this time, as shown in FIG. 3, X-rays 31 reflected from an inner wall surface 18 of the first collimator 10 adjacent the solar slit 7 will impinge upon an inner wall surface 18 thereof adjacent the sample piece 1 to generate disturbing rays 32, and/or X-rays 33 incident upon the inner wall surface 19 adjacent the solar slit 7 will generate fluorescent X-rays which subsequently impinge upon the inner wall surface 18 adjacent the sample piece 1 to thereby form disturbing rays 34. However, they will not become strong disturbing rays because reflection upon the inner wall surfaces 18 and 19 results in attenuation of the strength. In this way, since the first collimator 10 has no counterpart of the inner wall surface 16a employed in the prior art collimator 10 shown in FIG. 22, generation of the disturbing rays can advantageously be suppressed, resulting in further improvement of the S/N ratio.

It is to be noted that in the foregoing embodiment the first collimator 10 has been described and shown as having three apertures, the number of the apertures employed in the collimator 10 should be chosen in consideration of the sample pieces to be analyzed.

Hereinafter, the fluorescent X-ray analyzer according to a second preferred embodiment of the present invention will be described.

Figure 5:
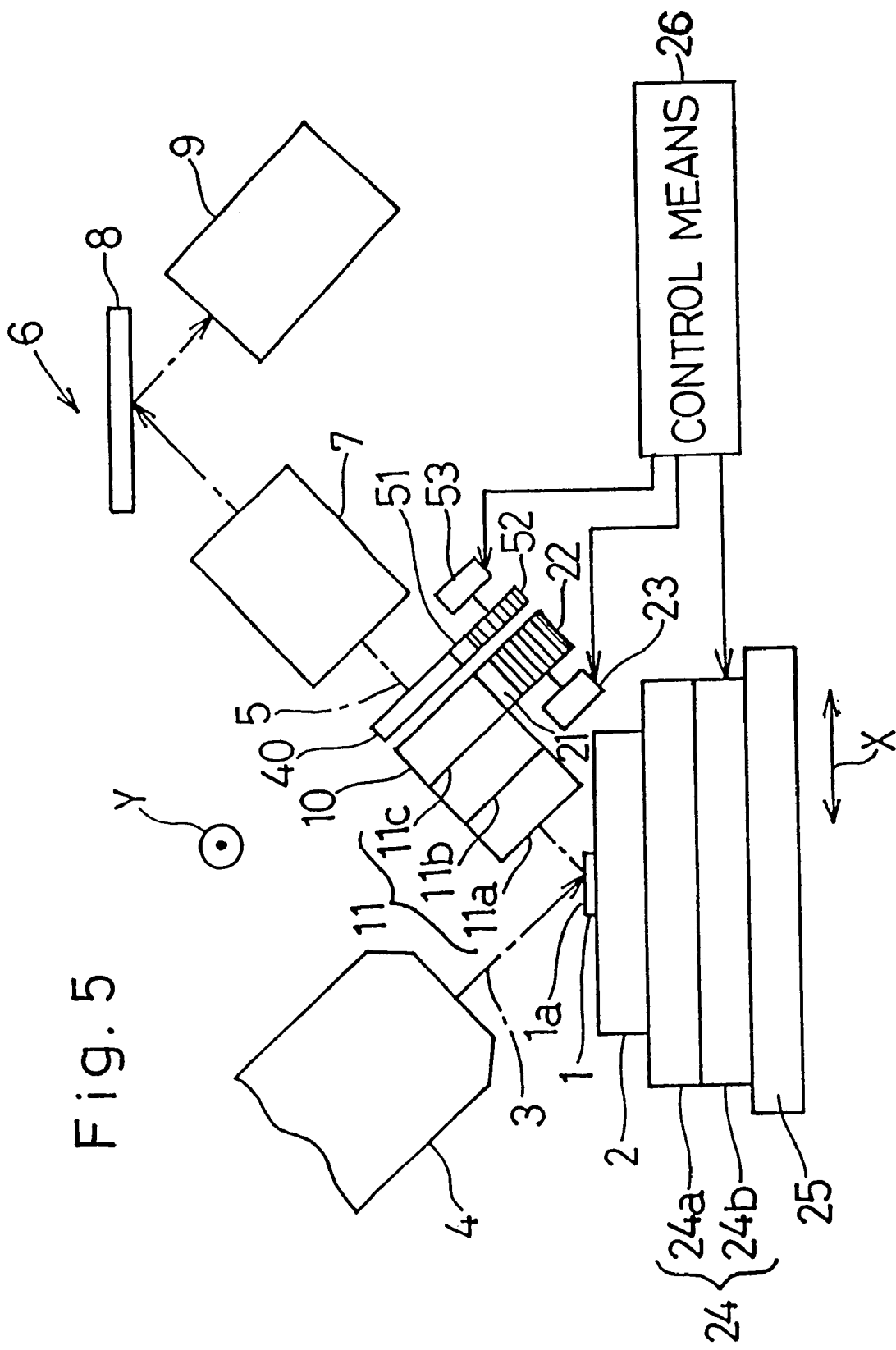
FIG. 5 is a schematic side view of the fluorescent X-ray analyzer according to a second preferred embodiment of the present invention.
Figure 6:
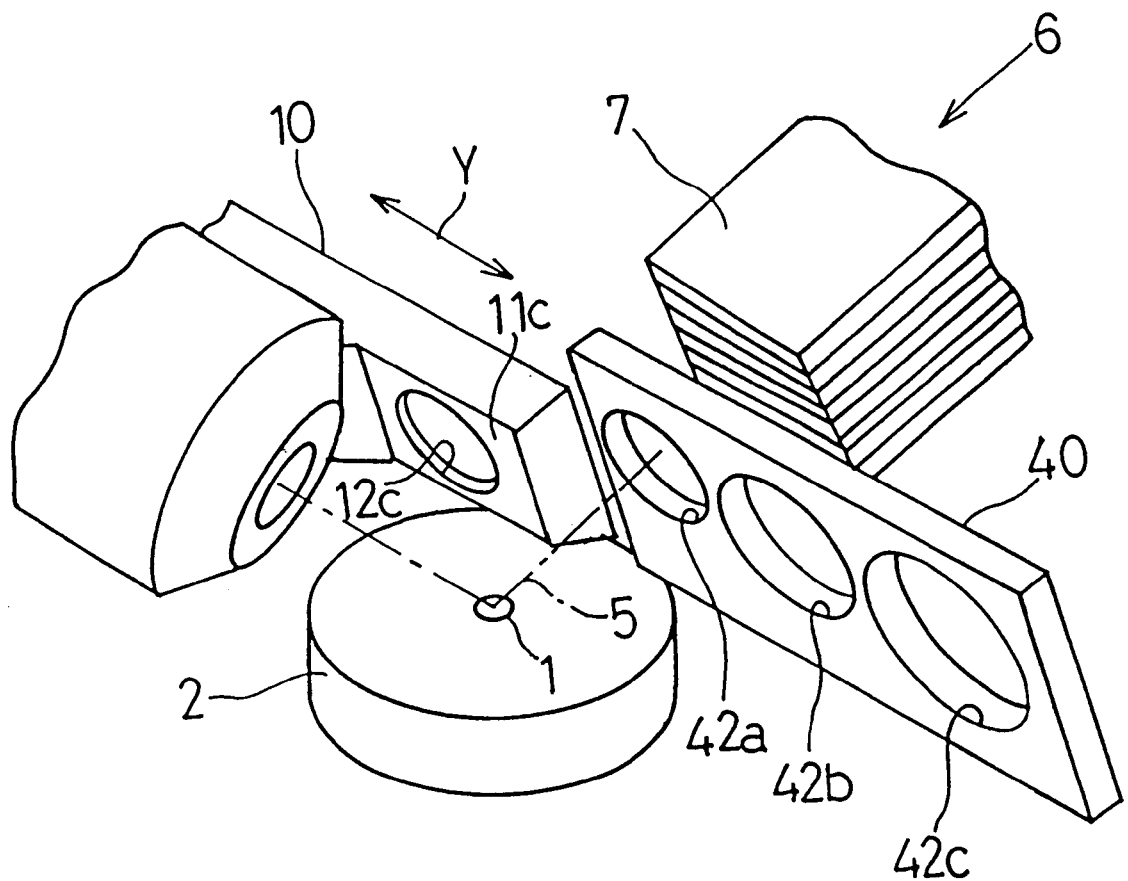
FIG. 6 is a schematic perspective view of an important portion of the fluorescent X-ray analyzer shown in FIG. 5.

The fluorescent X-ray analyzer according to the second embodiment of the present invention differs from that according to the previously described first embodiment in that a second collimator 40 is employed. This second collimator 40 is disposed between the first collimator 10 and the detecting means 6 as shown in FIG. 5. The second collimator 40 comprises an oblong plate member having defined therein one or more apertures of a diameter greater than any one of the apertures 12a to 12c in the first collimator 10 and is supported for movement in a direction shown by Y between inserted and retracted positions relative to the path of travel of the fluorescent X-rays 5. In the illustrated embodiment shown in FIG. 5, the number of the apertures in the second collimator 40 is three as indicated by 42a, 42b and 42c in FIG. 6.

The second collimator 40 is movably mounted on a guide member (not shown) and has a rack 51 secured to a bottom portion of the second collimator 40 and drivingly meshed with a pinion 52 fixedly mounted on a drive shaft of a stepping motor 53. Accordingly, when the stepping motor 53 is driven, the second collimator 40 can be slid along the guide member (not shown) in the direction Y in a manner similar to the first collimator 10.

The pattern of distribution B of the radiation intensity of the primary X-rays 3 on the imaginary irradiation plane shown in FIG. 23 is stored in the control means 26 as information on respective positions thereof with respect to the diameters D1, D2, D3, D4, D5 and D6 (wherein D1<D2<D3<D4<D5<D6) of the target area to be measured, or the optimum position at which the radiation intensity of the primary X-rays 3 towards the target area of the sample piece 1 can be maximized, is stored for each of the diameters D1, D2, D3, D4, D5 and D6. Likewise, the fact that the apertures corresponding to the diameters D1, D2 and D3 of the target areas to be measured are those of the first collimator 10 indicated by 12a, 12b and 12c, respectively, and the apertures corresponding to the diameters D4, D5 and D6 of the target areas to be measured are those of the second collimator 40 indicated by 42a, 42b and 42c is also stored in the control means 26.

Accordingly, where the diameter of the target area to be measured is large, one of the apertures 42a to 42c in the oblong plate member of the second collimator 40 is selected. In such case, although there is a relatively large distance between any one of the apertures 42a, 42b and 42c in the second collimator 40 and the target area to be measured, detection of the disturbing rays can be effectively and sufficiently avoided since the diameter of the target area to be measured is large. In this way, the provision of the second collimator 40 between the first collimator 10 and the detecting means 6 is effective to reduce the length of the first collimator 10 in the direction Y as compared with the length which the first collimator 10 would assume if six apertures were to be formed in a row in the first collimator 10. Reduction in length of the first collimator 10 is in turn effective to avoid any possible increase of the distance the first collimator 10 must move in the direction Y and also to compactize the first collimator 10. In the practice of the second embodiment of the present invention, although the second collimator 40 has been shown and described as having three apertures 42a to 42c, the number of the apertures in the second collimator 40 may not be always limited to three such as shown, but may be one or two or more than three and may thus be chosen depending on the number of respective sizes of the sample pieces to be analyzed.

The operation of the fluorescent X-ray analyzer designed according to the second embodiment of the present invention will now be described.

Assuming that the diameter of the target area to be measured is one of D1, D2 and D3, one of the apertures 12a to 12c in the first collimator 10 which corresponds to the diameter of the target area to be measured is brought into alignment with the path of travel of the fluorescent X-rays 5 between the sample piece 1 and the detecting means 6 as is the case with the first embodiment of the present invention. At this time, the second collimator 40 is retained in the retracted position out of the path of travel of the fluorescent X-rays 5.

In the event that the diameter of the target area of the sample piece 1 is large, and when instruction indicating that the diameter of the target area to be measured is one of D3, D4 and D5 is inputted to the control means 26, the control means 26 controls the X-Y stage 24 so that the sample table 2 can be moved to a position at which the radiation intensity of the primary X-rays 3 towards the target area of the sample piece 1 to be measured is maximum. Simultaneously therewith, the control means 26 controls the stepping motor 53 so that one of the apertures 42a, 42b and 42c in the second collimator 40 which corresponds to the diameter D3, D4 or D5 of the target area of the sample piece 1 to be measured can be selected. As a result of rotation of the stepping motor 53, the second collimator 40 is moved in the direction Y to bring the selected aperture 42a, 42b or 42c in the second collimator 40 in alignment with the path of travel of the fluorescent X-rays 5 between the sample piece 1 and the detecting means 6. At this time, the first collimator 10 is moved to the retracted position out of the path of travel of the fluorescent X-rays 5.

As discussed above, by alternately moving the first and second collimators 10 and 40, the distance of movement of any one of the first and second collimators 10 and 40 can suffice to be small as compared with that exhibited when the single collimator is employed.

Figure 7A:
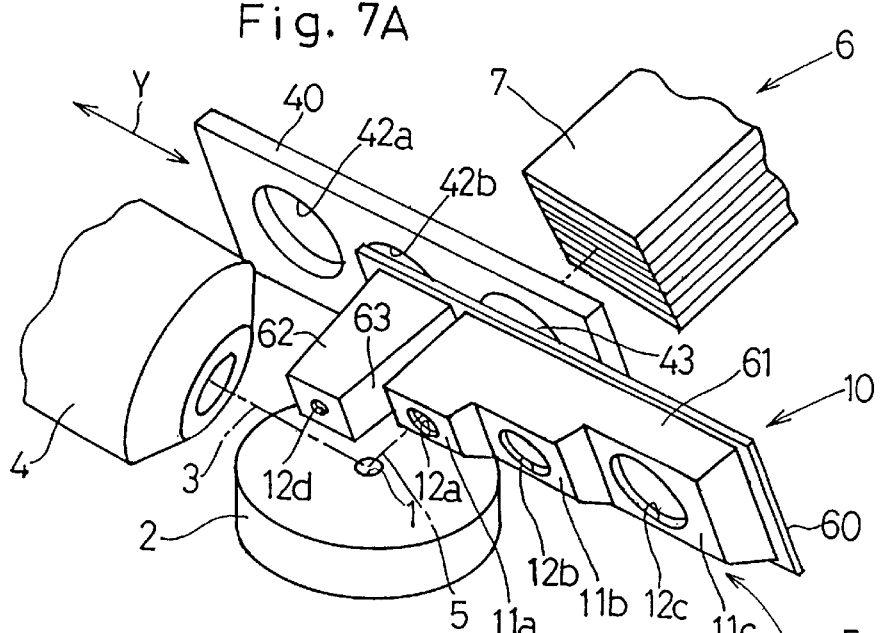
FIG. 7A is a schematic perspective view of the fluorescent X-ray analyzer according to a third preferred embodiment of the present invention, showing an important portion thereof.
Figure 7B:
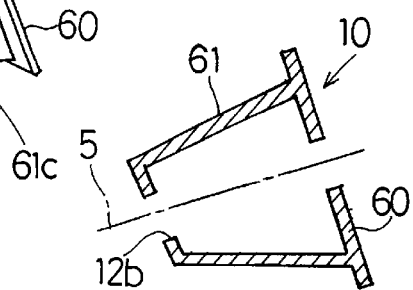
FIG. 7B is a schematic longitudinal sectional view of the first collimator employed in the fluorescent X-ray analyzer shown in FIG. 7A.
Figure 8:
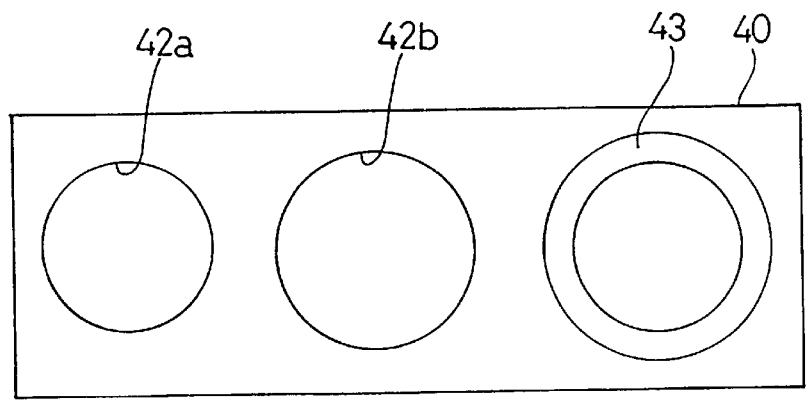
FIG. 8 is a schematic front elevational view of a second collimator employed in the fluorescent X-ray analyzer according to the third preferred embodiment of the present invention.

With particular reference to FIGS. 7A to 8, the fluorescent X-ray analyzer according to a third preferred embodiment of the present invention will be described.

Even in the fluorescent X-ray analyzer according to the third embodiment of the present invention as best shown in FIG. 7A, the first collimator 10, the second collimator 40 and the position of the sample piece 1 are controlled by the control means 26 as is the case with that in the second embodiment of the present invention shown in FIG. 5. As best shown in FIG. 7B, the first collimator 10 includes a single, generally rectangular substrate 60 which forms a wall facing towards the solar slit 7. This single substrate 60 is formed with a first hollow projection 61 and a second hollow projection 62 positioned laterally of the first hollow projection 61 in a direction conforming to the longitudinal axis of the single substrate 60. The first hollow projection 61 has a front wall 61c stepped to provide front wall segments 11a, 11b and 11c each having the corresponding aperture 12a, 12b or 12c defined therein in correspondence with the size of the shape of an analyzing surface of the sample piece 1. The second hollow projection 62 is of a generally truncated pyramid shape and is formed with a aperture 12d of a diameter smaller than the diameter of any of the apertures 12a to 12c. The second hollow projection 62 protrude from the single substrate 60 a larger distance than the first hollow projection 61.

Although in the illustrated embodiment the second hollow projection 62 is of a generally truncated pyramid shape, it may be of a generally truncated conical shape or a cylindrical or tubular shape.

The second hollow projection 62 has a side wall 63 which may have a window defined therein, in which case a portion of the X-rays entering the aperture 12d will emerge outwardly from the second hollow projection 62 through the window. Accordingly, the disturbing rays such as the fluorescent X-rays and/or the scattering X-rays which would be generated as a result of impingement of the fluorescent X-rays upon the inner wall surface of the second hollow projection 62 would hardly occur, accompanied by a further improvement of the S/N ratio.

The substrate 60 of the first collimator 10 has defined therein auxiliary apertures of respective diameters equal to or greater than those of the apertures 12a, 12b and 12c, which correspond respectively to the apertures 14a, 14b and 14c shown in FIG. 3 and which are so arranged that when the sample piece 1 is viewed from the detecting means 6, only the sample piece 1 can be encompassed.

The second collimator 40 comprises a generally oblong flat plate member having defined therein apertures 42a and 42b of a diameter greater than that of the apertures 12a, 12b, 12c and 12d in the first and second hollow projections 61 and 62. As best shown in FIG. 8, the second collimator 40 is also provided with an energy dispersive detector, for example, SSD (solid state detector) 43 positioned laterally of the apertures 42a and 42b for detecting the fluorescent X-rays 5 which have been partially cut off by one of the apertures 12a to 12d in the first collimator 10.

The fluorescent X-ray analyzer according to the third embodiment of the present invention operates in the following manner.

The manner in which the fluorescent X-rays are partially cut off by selecting one of the apertures 12a to 12c in the first collimator 10 or one of the apertures 42a and 42b in the second collimator 40 is substantially similar to that employed in the practice of any one of the first and second embodiments of the present invention.

Where the target area of the sample piece 1 to be measured is small, the aperture 12d in the second hollow projection 62 is selected, in which case the second collimator 40 is moved in the direction Y to assume a potion rearwards of the aperture 12d and the fluorescent X-rays 5 passing through the aperture 12d are detected by the SSD 43. The SSD 43 is of an energy dispersive type and is capable of examining roughly the X-ray spectra from the sample piece without monochromatizing. Even when any one of the apertures 12a to 12c in the first hollow projection 61, the fluorescent X-rays passing through such one of the apertures 12a to 12c can be detected by the SSD 43. In such case, after the spectra have been roughly examined by the SSD 43, in a manner similar to that in any one of the first and second embodiments, the use may be made of the detecting means 6 to determine a particular wavelength range according to the parallel beam method or the focusing method.

Figure 9:
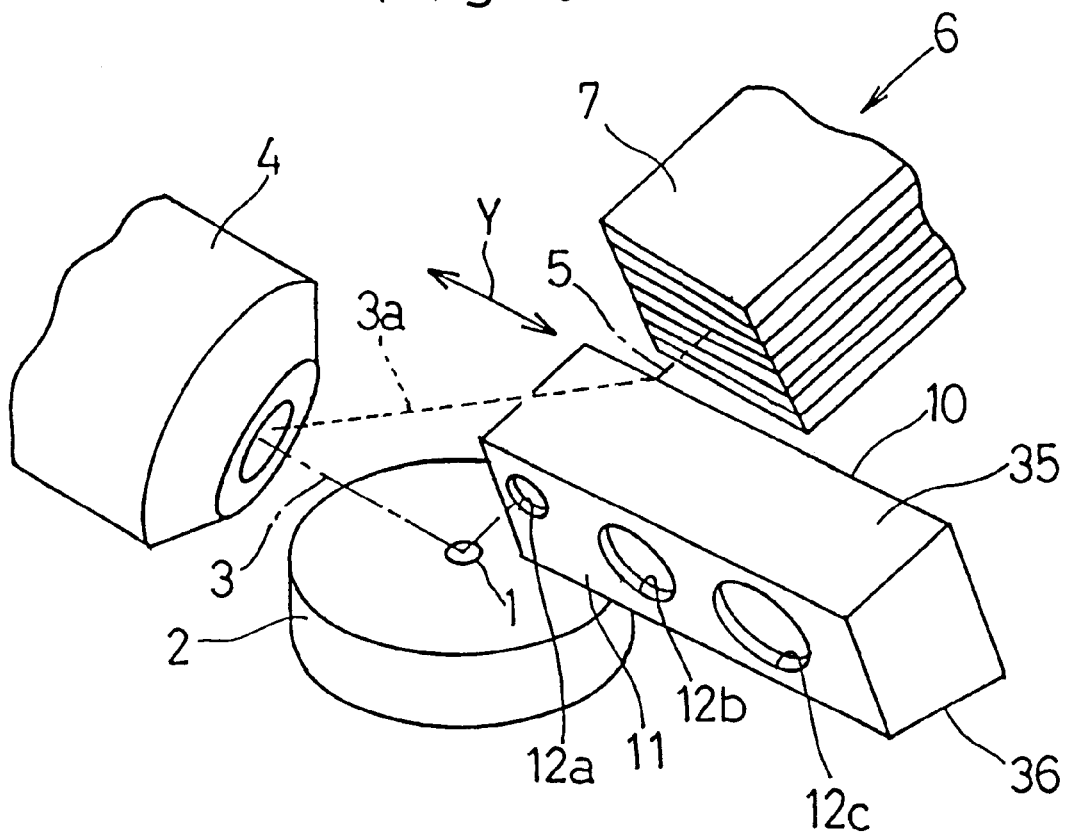
FIG. 9 is a schematic perspective view of the fluorescent X-ray analyzer according to a fourth preferred embodiment of the present invention, showing an important portion thereof.
Figure 10:
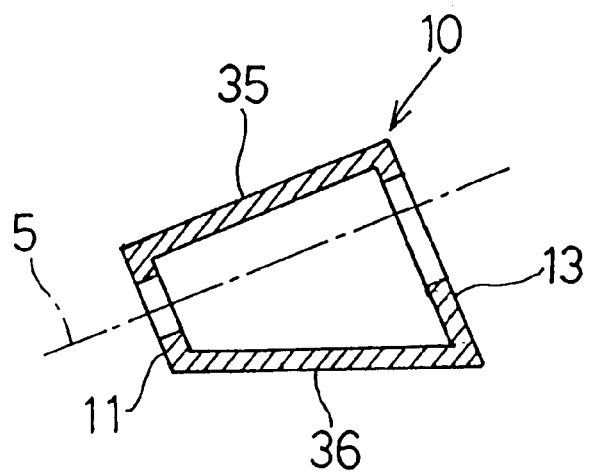
FIG. 10 is a schematic longitudinal sectional view of a first collimator employed in the fluorescent X-ray analyzer shown in FIG. 9.

The fluorescent X-ray analyzer according to a fourth preferred embodiment of the present invention is shown in FIGS. 9 and 10.

While a portion of the structure of the fluorescent X-ray analyzer according to the fourth embodiment of the present invention which is similar to that according to the first embodiment of the present invention will not be described in detail for the sake of brevity, only the difference therebetween will be described. As shown in FIG. 9, the first collimator 10 is disposed on the path of travel of the fluorescent X-rays 5 between the sample piece 1 and the detecting means 6. The first collimator 10 includes a front wall 11 adjacent the sample piece 1 and having a row of apertures 12a, 12b and 12c defined therein, a rear wall 13 adjacent the detecting means 6 as shown in FIG. 10, and a top wall 35 which serves as respective shielding wall, and a bottom wall 36. The front wall 11 is close to the sample piece 1, at least a portion thereof being positioned within a region in which the primary X-rays 3 generated from the X-ray source 4 radiate. The top wall 35 serves to prevent the primary X-rays 3 irradiated from the X-ray source 4 to enter directly rearwards of the front wall 11, that is, the path of travel of the fluorescent X-rays 5 from the side of the detecting means 6, without being reflected. Without the top wall 35 which is the shielding wall, the primary X-rays shown by the dotted line 3a will enter the path of travel of the fluorescent X-rays 5 and will hence become disturbing rays which would in turn result in reduction of the S/N ratio.

The fluorescent X-ray analyzer according to this fourth embodiment of the present invention, although provided with the bottom and rear walls 36 and 13, may not always require the bottom and rear walls 36 and 13.

Figure 22:
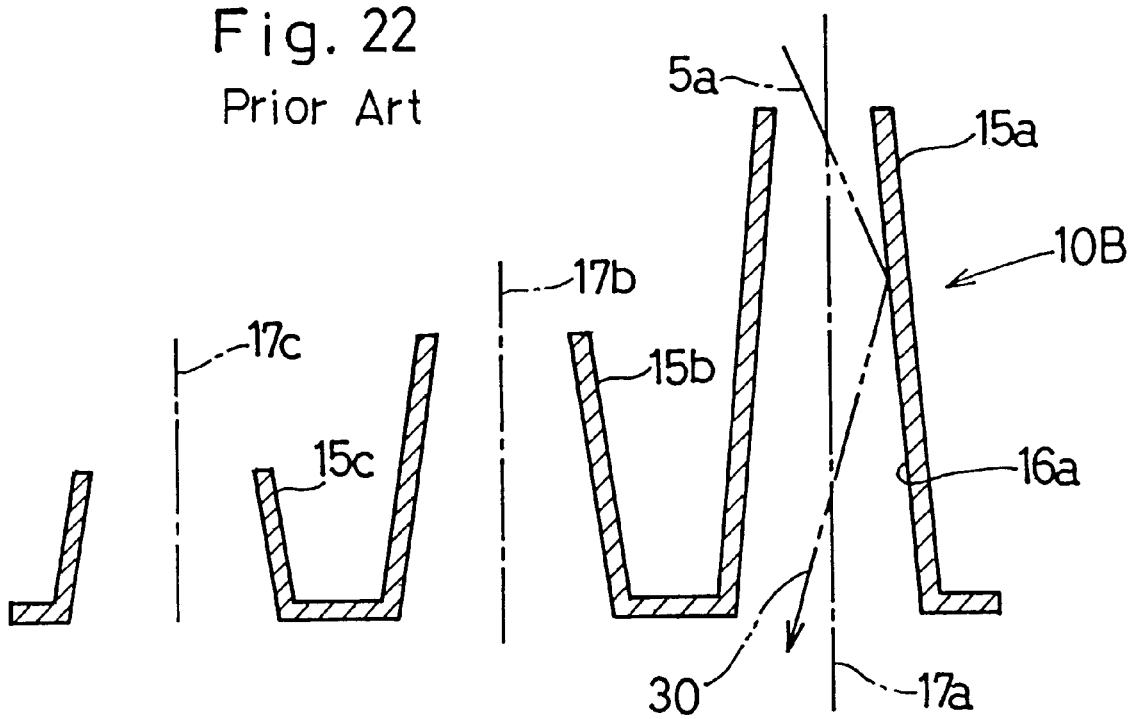
FIG. 22 is a schematic transverse sectional view, on an enlarged scale, showing a collimator employed in the prior art fluorescent X-ray analyzer shown in FIG. 21.

The first collimator 10 employed in the fourth embodiment of the present invention is of a substantially hollow structure of a rectangular parallelopiped shape wherein the apertures 12a, 12b and 12c are formed in the front wall 11 adjacent the sample piece 1 and the rear wall 13 adjacent the detecting means 6 and is therefore each to fabricate. Also, since as is the case with the first embodiment no counterpart of the inner wall surface 16a of the prior art collimator 10 shown in FIG. 22 is employed, generation of the disturbing rays can be suppressed with the S/N ratio consequently improved.

In the fourth embodiment, the bottom wall 36 is so inclined as to displace upwardly towards the front and, therefore, the first collimator 10 can be brought close towards the sample piece 1 without contacting the sample table 2 with the S/N ratio consequently improved.

Although in this embodiment, a so-called top radiating system is employed in which the primary X-rays 3 are irradiated towards the sample piece 1 from top, if a so-called bottom radiating system in which the primary X-rays are irradiated towards the sample piece 1 from below is desired to be employed, the first collimator 10 has to be disposed in a fashion turned upside down.

FIGS. 11 to 14 illustrate the fluorescent X-ray analyzer according to a fifth embodiment of the present invention, reference to which will now be made.

Figure 11:
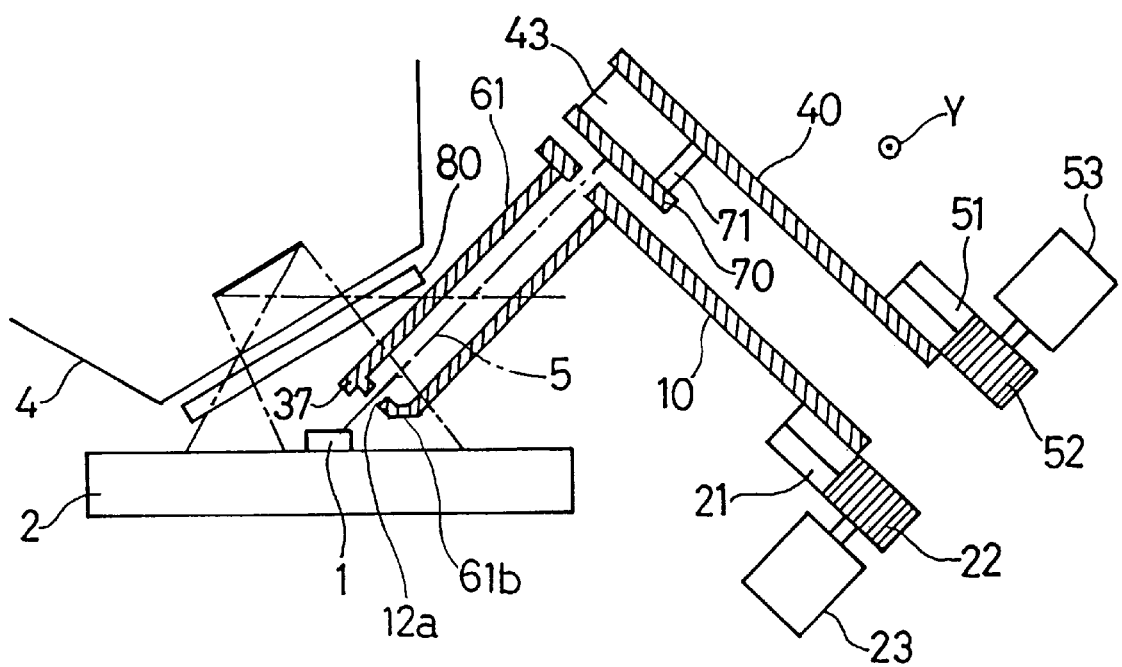
FIG. 11 is a schematic longitudinal sectional view of the fluorescent X-ray analyzer according to a fifth preferred embodiment of the present invention, showing an important portion thereof.

While a portion of the structure of the fluorescent X-ray analyzer according to the fifth embodiment of the present invention which is similar to that according to the third embodiment of the present invention will not be described in detail for the sake of brevity, only the difference therebetween will be described. As shown in FIG. 11 in a sectional representation of a portion of the fluorescent X-ray analyzer, the fluorescent X-ray analyzer comprises the first collimator 10 and the second collimator 40. The first collimator 10 is movable in the direction Y as a slider (not shown) fitted to the first collimator 10 slides along a guide bar (not shown) extending in the direction Y perpendicular to the plane of the sheet of the drawing. A rack 21 split into front and rear components is secured to a bottom portion of the first collimator 10 and is drivingly meshed with a pinion 22 rigidly mounted on a drive shaft of a stepping motor 23.

Figure 12:
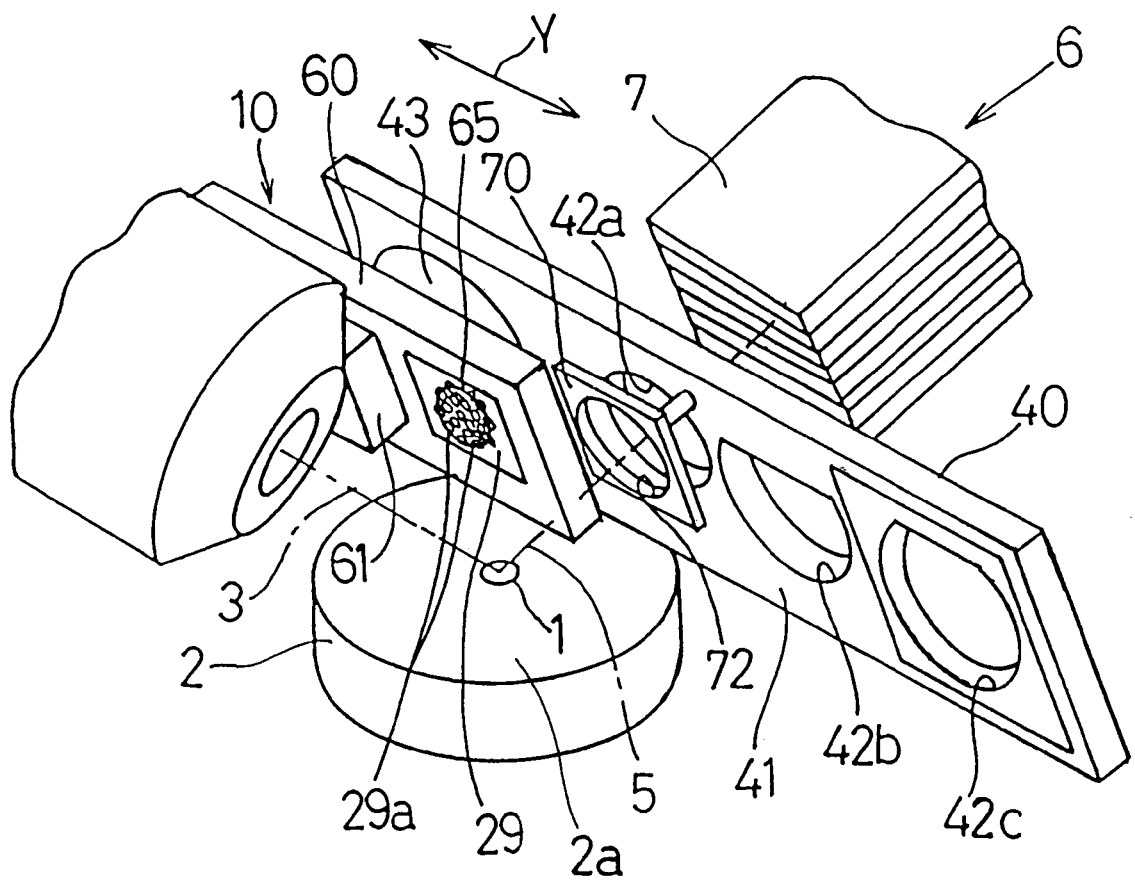
FIG. 12 is a schematic perspective view of that important portion of the fluorescent X-ray analyzer shown in FIG. 11.

As shown in FIG. 12, the second collimator 40 has a plurality of, for example, three apertures 42a, 42b and 42c of varying diameters and includes a SSD 43 positioned laterally of the row of the apertures 42a to 42c. The SSD 43 is covered by a covering (not shown) to prevent the scattering rays from impinging thereupon. Each of the apertures 42b and 42c in the second collimator 40 shown in FIG. 12 is of a shape in which a top portion of the circle depicted by the respective aperture is depleted so that the disturbing X-rays radiated from the X-ray tube and/or the disturbing X-rays reflected from a filter holder 80 installed in front of the X-ray tube forming the X-ray source 4 shown in FIG. 11 can be prevented from entering the path of travel of the fluorescent X-rays 5.

A third collimator 70 is disposed between the first collimator 10 and the second collimator 40. This third collimator 70 is fitted to the second collimator 40 by means of, for example, a plurality of set screws 71. A aperture 72 in the third collimator 70 as shown in FIG. 12 is of a diameter smaller than that of any of the apertures 42a to 42c in the second collimator 40. The use of the third collimator 70 nearer towards the sample 1 than the second collimator 40 is effective to shield the disturbing rays as compared with the use of only the aperture 42a in the second collimator 40, thereby to improve the S/N ratio.

As is the case with the first collimator 10, even the second collimator 40 shown in FIG. 11 is movable in the direction Y as the slider (not shown) slides along the guide bar (not shown) extending in the direction Y perpendicular to the plane of the sheet of the drawing. A rack 51 split into front and rear components is secured to the second collimator 40 and is drivingly meshed with a pinion 52 rigidly mounted on a drive shaft of a stepping motor 53.

Figure 13A:
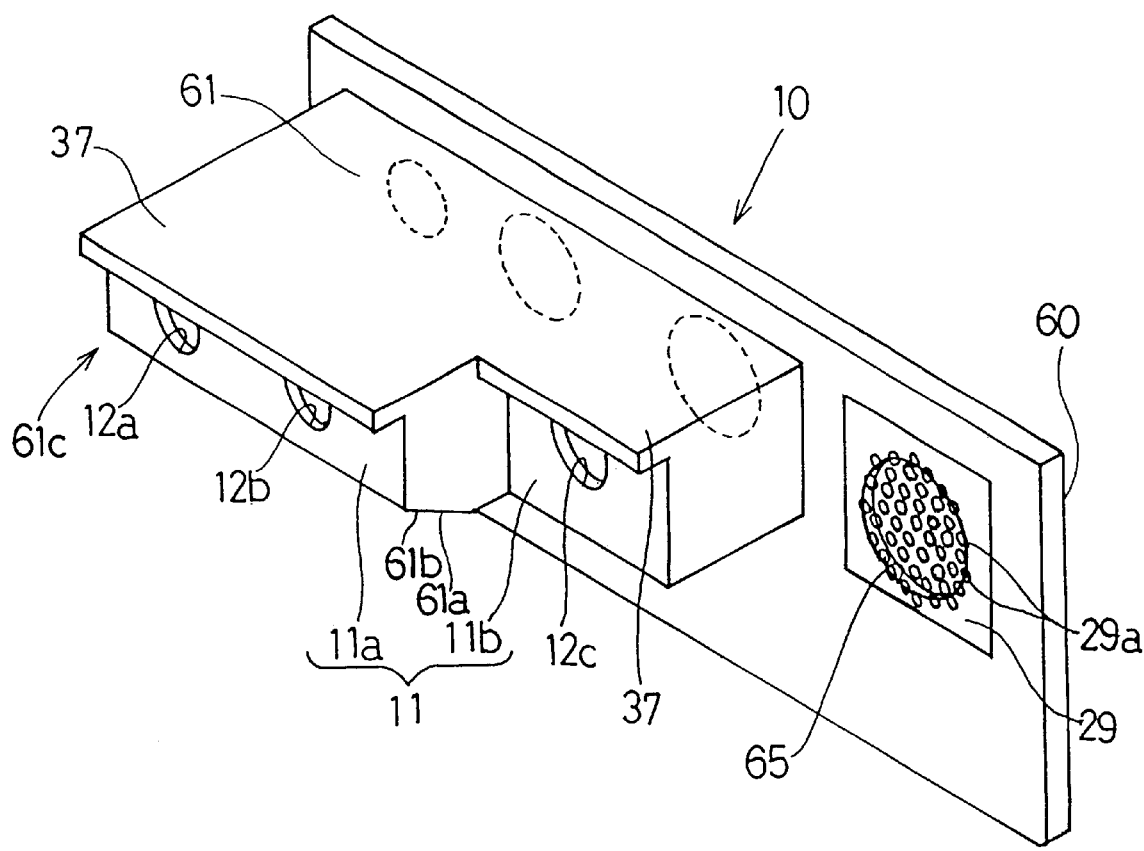
FIG. 13A is a schematic perspective view of a first collimator employed in the fluorescent X-ray analyzer shown in FIG. 11.

As shown in FIG. 12, the first collimator 10 is so arranged as to encompass the fluorescent X-rays 5 in a direction inclined relative to the sample table 2 supporting the sample piece 1 thereon. The first collimator 10 comprises, as shown in FIG. 13A in detail, a single substrate 60 forming a wall adjacent the solar slit 7 and provided with a hollow projection 61. A wall 11 of the hollow projection 61 adjacent the sample piece 1 is stepped in two stages including a wall segment 11a close to the sample piece 1 and a wall segment 1b remote from the sample piece 1. The wall segment 11a is formed with two apertures 12a and 12b while the wall segment 11b is formed with a aperture 12c of a large diameter. A lower corner area 61a of the hollow projection 61 which confronts the sample table 2 is chamfered to define a slanted surface 61b generally parallel to a surface 2a of the sample table 2. Because of the slanted surface 61b, the hollow projection 61 will not interfere with the sample table 2 even though the apertures 12a and 12b in the hollow projection 61 are brought close to the target area of the sample piece 1 to be measured. The single substrate 60 of the first collimator 10 is also formed with a aperture 65 of a diameter equal to or greater than one of the apertures 42a to 42c in the second collimator 40 which has the greatest diameter, which aperture 65 is positioned laterally of the hollow projection 61.

Figure 13B:
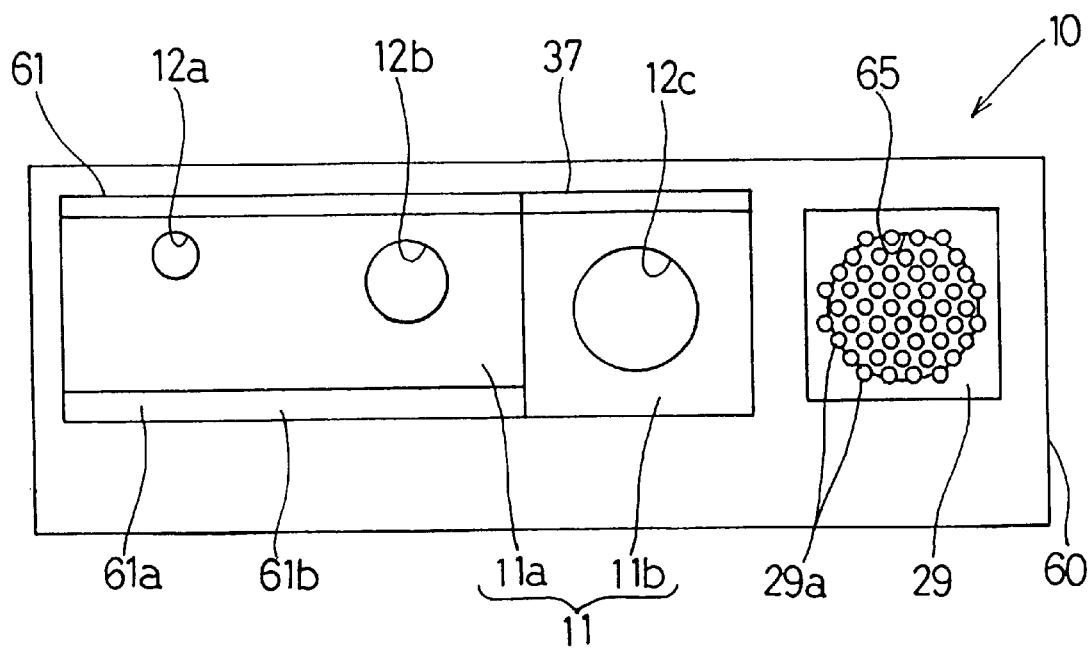
FIG. 13B is a schematic front elevational view of the first collimator employed in the fluorescent X-ray analyzer shown in FIG. 11.
Figure 14:
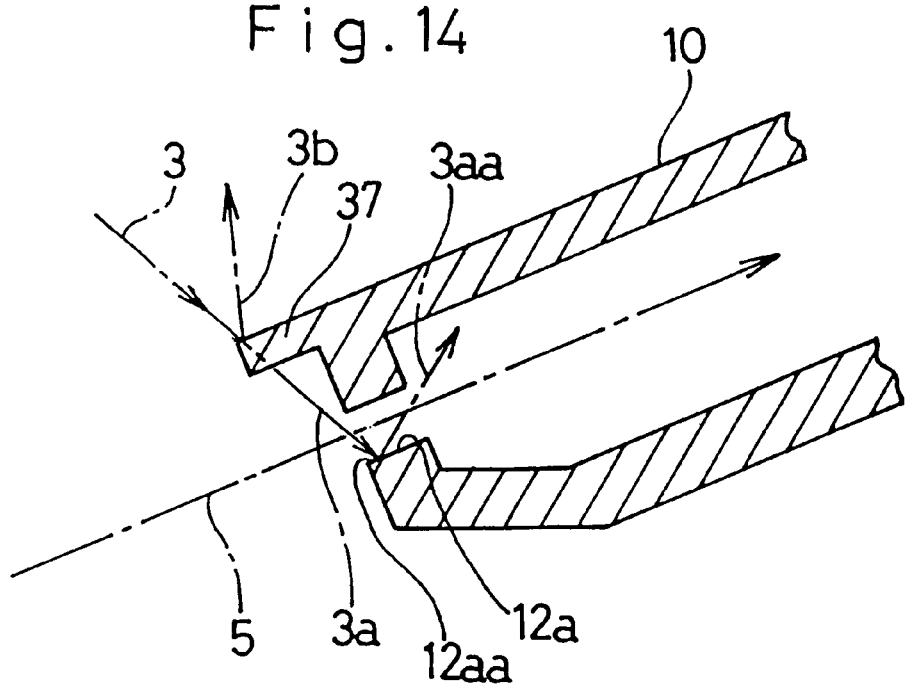
FIG. 14 is a longitudinal sectional view, on an enlarged scale, showing a portion of the first collimator employed in the fluorescent X-ray analyzer shown in FIG. 11.

As shown in FIG. 13B, the aperture 65 formed in the substrate 60 of the first collimator 10 is fitted with an attenuator 29. This attenuator 29 comprises a flat plate formed with a plurality of holes 29a for passage therethrough of the fluorescent X-rays. When the fluorescent X-rays are to be analyzed by selecting one of the apertures 42a to 42c in the second collimator 40 and by impinging the fluorescent X-rays, which have passed through this aperture, upon the fluorescent X-ray detecting means 6, it is often observed that, since the sample to be measured contains a particular element in a large amount, the intensity of the fluorescent X-rays tends to be excessively high. In such case, the first collimator 10 is moved in a direction shown by Y (FIG. 12) so that the aperture 65 fitted with the attenuator 29 may be disposed on the path of travel of the fluorescent X-rays 5 so as to align with any one of the apertures 42a to 42c in the second collimator 40. In this way, the intensity of the fluorescent X-rays incident upon the detecting means 6 through the first and second collimators 10 and 40 can be reduced.

As shown in FIG. 13A, the first collimator 10 has a visor 37 serving as a shielding provided at a front side of the front wall 11 of the hollow projection 61 for preventing the primary X-rays 3, emitted from the X-ray source 4, from entering a front edge of the apertures 12a to 12c, that is, the open edge adjacent the sample piece 1. The visor 37 may be in the form of a separate flat plate member secured to the first collimator 10, or may be an unitary structure of the first collimator 10 having been formed by grinding. As shown on an enlarged scale in FIG. 14, without the visor 37, the primary X-rays 3 will impinge upon an open edge 12aa of the aperture 12a as shown by the arrow 3a and will then be reflected in a manner as shown by the arrow 3aa so as to enter the passage for the fluorescent X-rays 5, thereby forming disturbing rays. In contrast thereto, since the first collimator 10 is provided with the visor 37 as hereinabove described, the primary X-rays 3 can be reflected by an upper surface of the visor 37 and will not therefore form disturbing rays.

A sixth preferred embodiment of the present invention will now be described with particular reference to FIG. 15.

Figure 15:
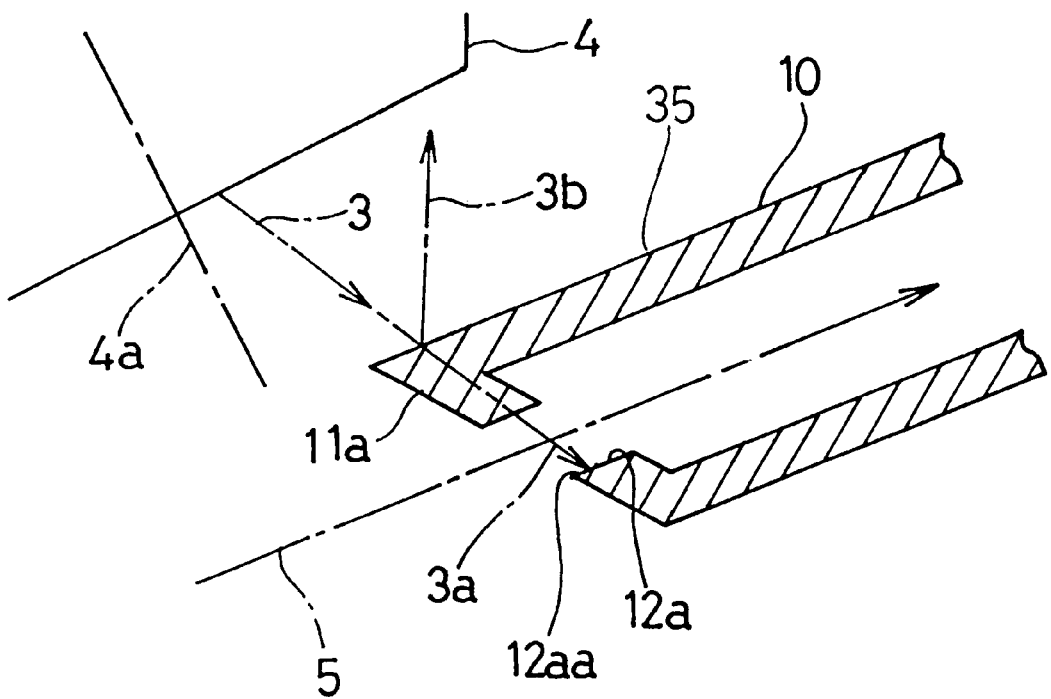
FIG. 15 is a longitudinal sectional view, on an enlarged scale, showing a portion of a first collimator employed in the fluorescent X-ray analyzer according to a sixth preferred embodiment of the present invention.

The fluorescent X-ray analyzer according to the sixth embodiment differs from that according to the fifth embodiment in that in the embodiment shown in FIG. 15 no visor such as indicated by 37 and used in the first collimator 10 in the fifth embodiment is employed and, instead, an upper portion of the front wall 11a adjacent the X-ray source 4 is inclined in a direction towards a center axis 4a of the X-ray source 4 to thereby prevent the primary X-rays 3, emitted by the X-ray source 4, from entering the aperture 12a directly. In this way, the primary X-rays 3 will not impinge upon the open edge 12aa of the aperture 12a as shown by the arrow 3a, but will rather be reflected by the upper surface of the upper wall 10 as shown by the arrow 3b without forming the disturbing rays that may interfere with the fluorescent X-rays 5.

In contrast thereto, in the case of a so-called bottom radiating system, the first collimator 10 has to be disposed in a fashion turned upside down.

Figure 16:
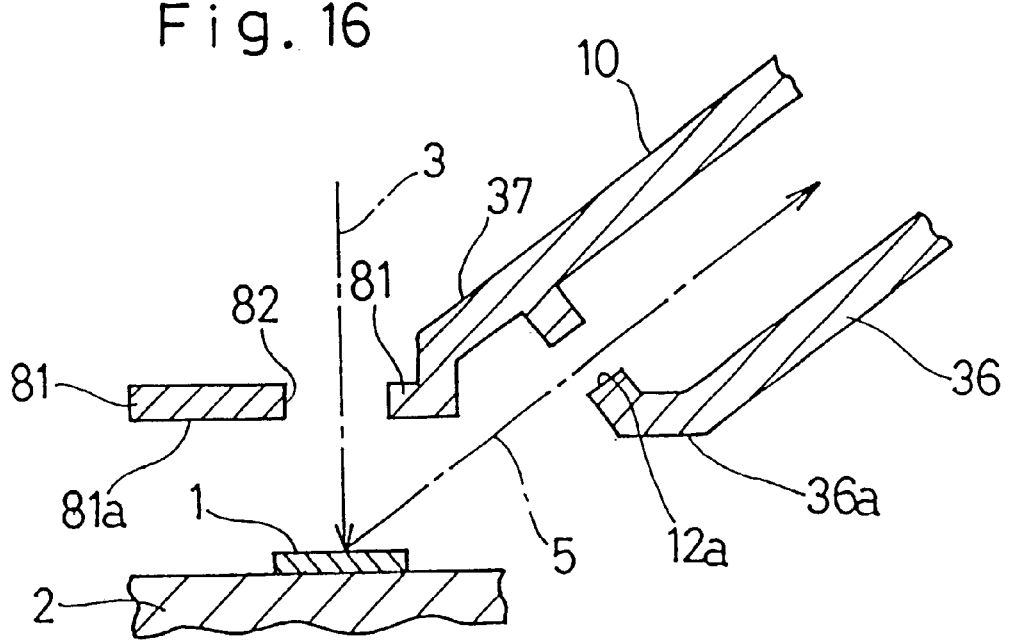
FIG. 16 is a longitudinal sectional view, on an enlarged scale, showing a portion of a first collimator employed in the fluorescent X-ray analyzer according to a seventh preferred embodiment of the present invention.
Figure 17:
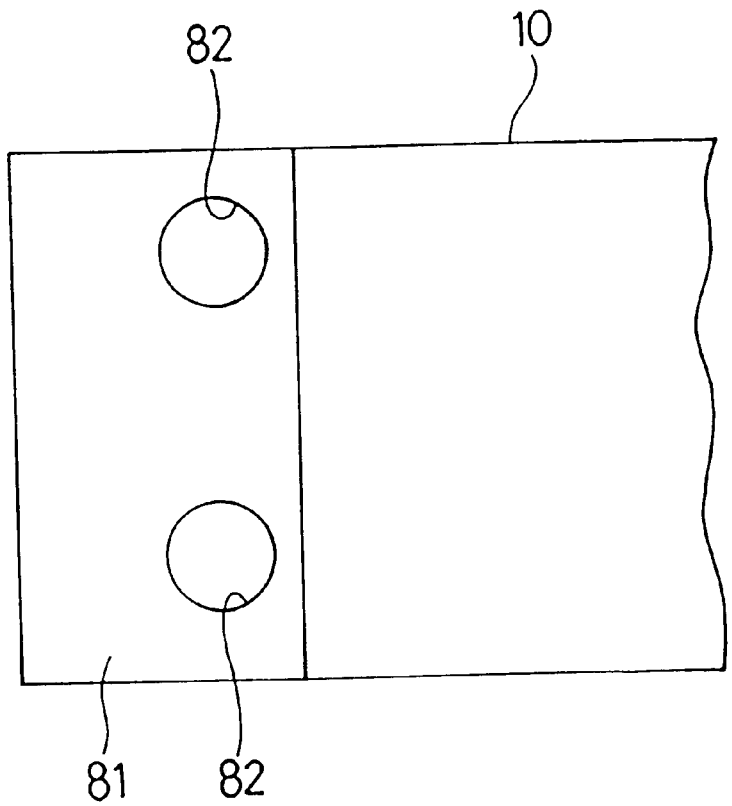
FIG. 17 is a schematic top plan view of the first collimator employed in the fluorescent X-ray analyzer according to the seventh preferred embodiment of the present invention.

FIGS. 16 and 17 pertains to a seventh preferred embodiment of the present invention which will be described hereinafter.

The fluorescent X-ray analyzer according to the seventh embodiment differs from that according to the fifth embodiment in that as shown in FIGS. 16 and 17, the visor 37 of the first collimator 10 has an extension 81 where a primary X-ray aperture 82 of a round configuration is defined for partially cutting off the primary X-rays 3, emitted from the X-ray source, so as to allow the partially cut off primary X-rays 3 to impinge upon the sample piece 1. This extension 81 serves as a shielding member to thereby prevent the primary X-rays 3 from entering the aperture 12a. Since the primary X-rays 3 are partially cut off as it passes through the primary X-ray aperture 82, and is then impinged upon the sample piece 1, generation of the fluorescent X-rays from a portion of the sample table 2 around the sample piece 1 can advantageously suppressed to increase the measurement accuracy. Also, it is preferred that the extension 81 is so positioned as to allow an undersurface 81a of the extension 81 to be as close to the sample piece 1 as possible, that is, as to allow the undersurface 81a to be sufficiently below without allowing the extension 81 to interfere the path of travel of the fluorescent X-rays 5, for example, at a horizontal plane substantially flush with the lowest surface 36a of the first collimator 10. Although in the illustrated embodiment, the primary X-ray aperture 82 and the first collimator 10 are of an unitary structure, they may be separate from each other.

The fluorescent X-ray analyzer according to an eighth preferred embodiment of the present invention will now be described with reference to FIG. 18.

Figure 18:
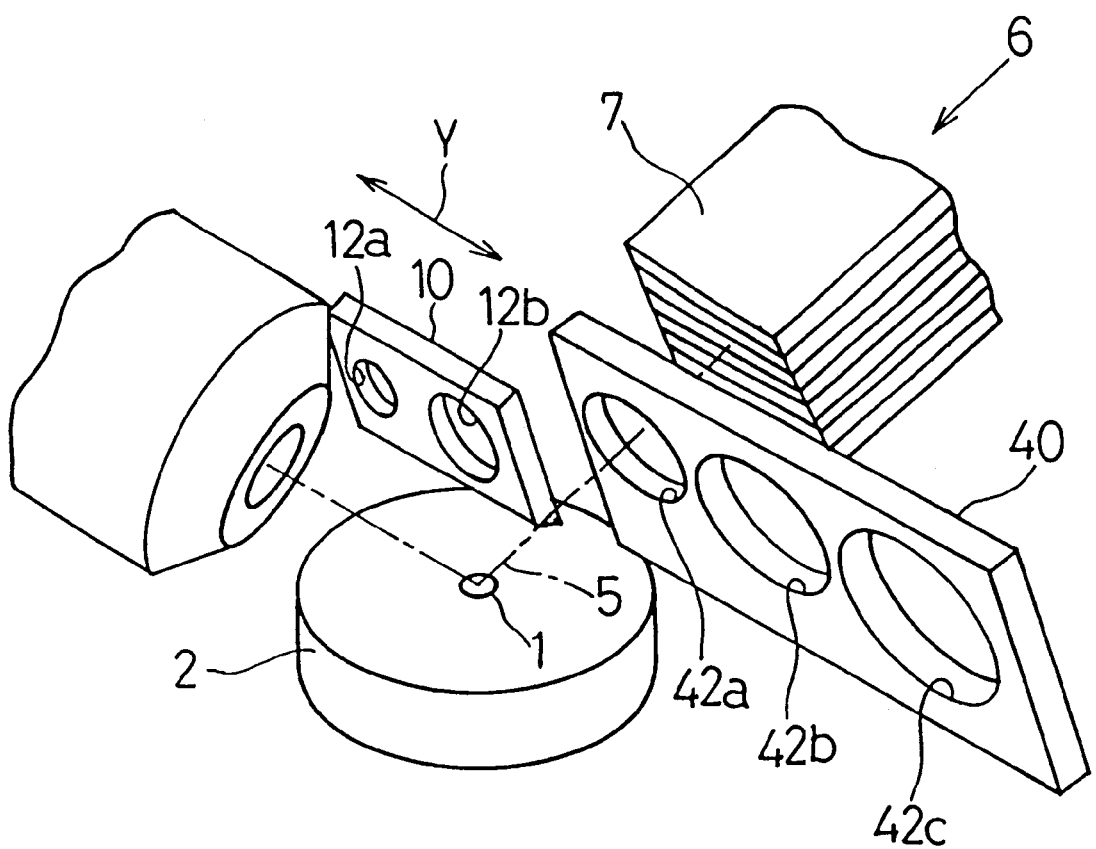
FIG. 18 is a schematic perspective view of the fluorescent X-ray analyzer according to an eighth preferred embodiment of the present invention, showing an important portion thereof.
Figure 19:
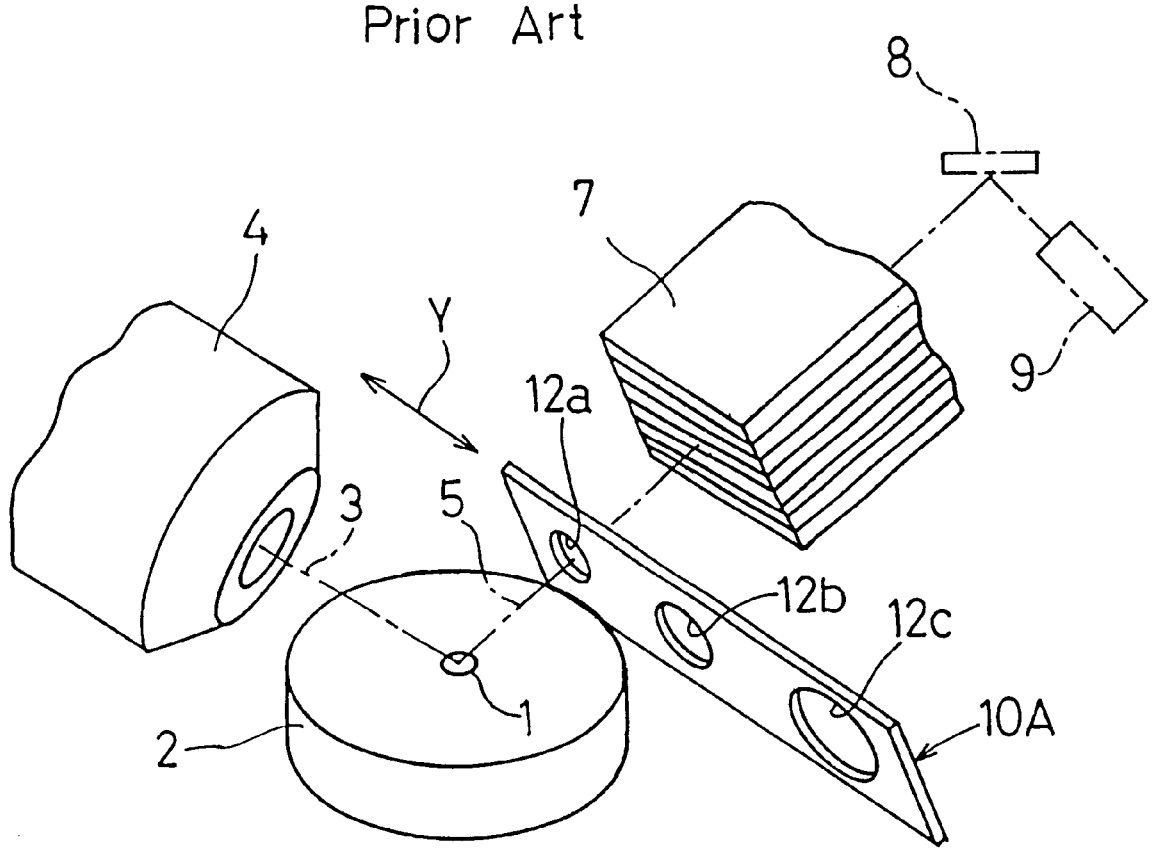
FIG. 19 is a schematic perspective view of one example of the prior art fluorescent X-ray analyzer, showing an important portion thereof.
Figure 20A:
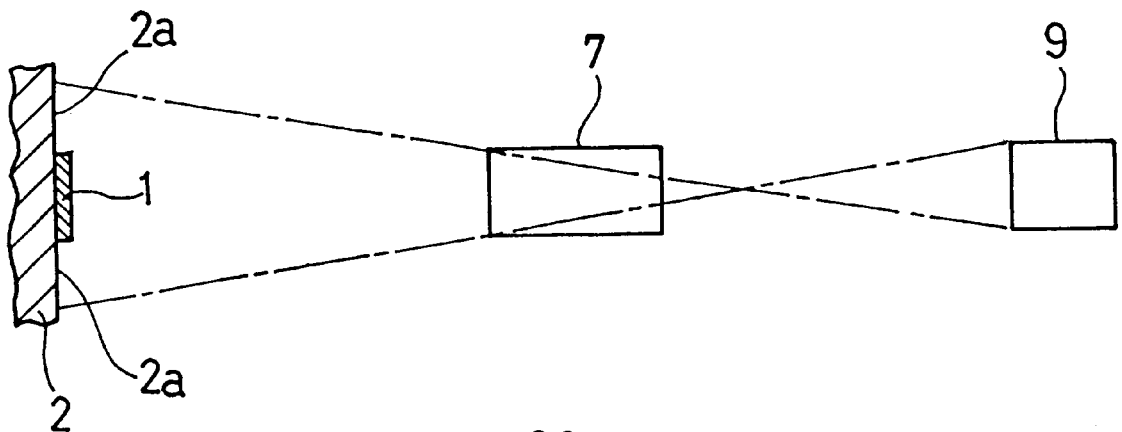
FIG. 20A is a schematic side sectional view of the prior art fluorescent X-ray analyzer shown in FIG. 19, showing how the fluorescent X-rays can be detected by a detector when no collimator is used.
Figure 20B:
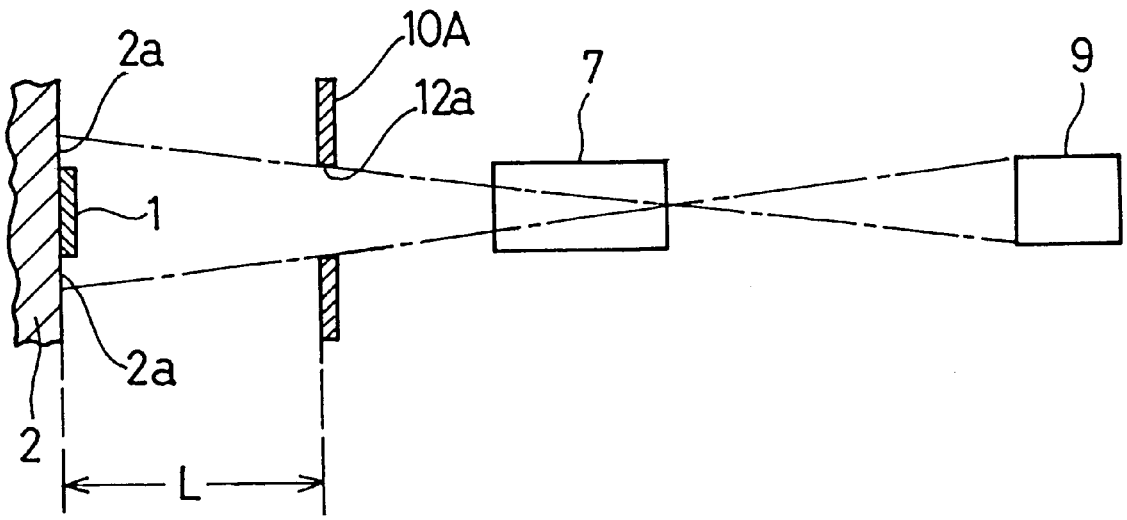
FIG. 20B is a schematic side sectional view of the prior art fluorescent X-ray analyzer shown in FIG. 19, showing how the fluorescent X-rays can be detected by a detector when the collimator is used.
Figure 21:
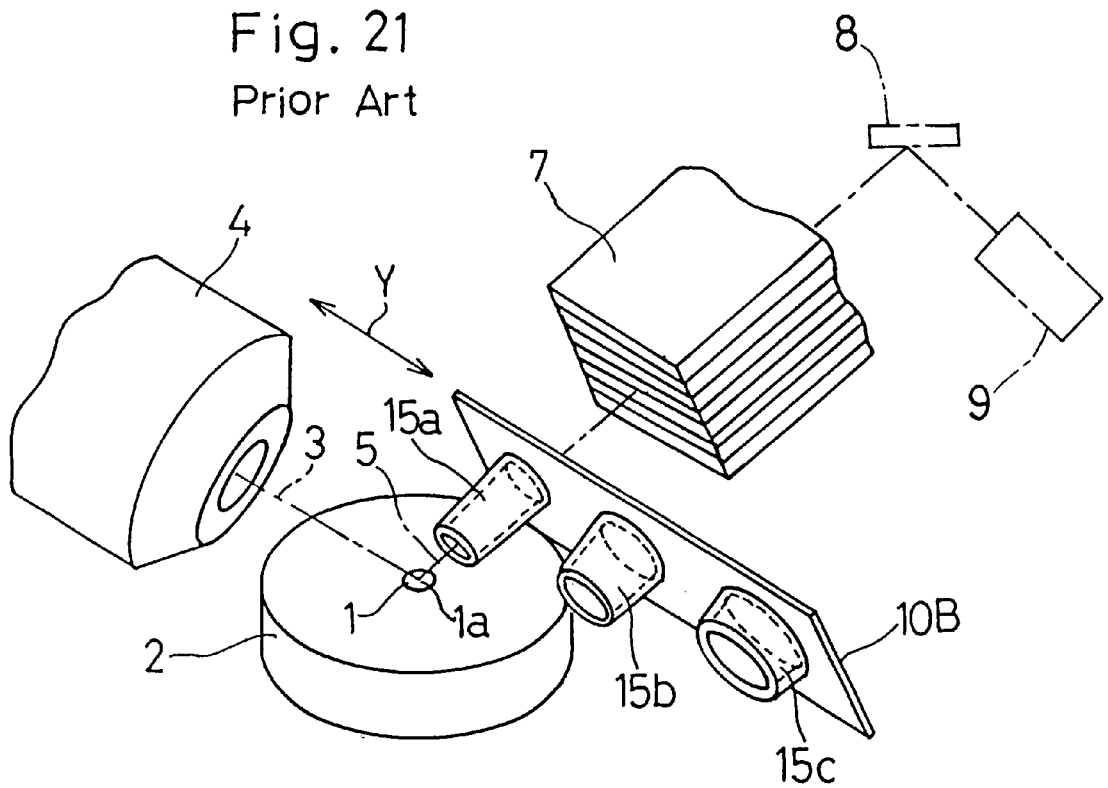
FIG. 21 is a schematic perspective view of another example of the prior art fluorescent X-ray analyzer, showing an important portion thereof.

The fluorescent X-ray analyzer according to the eighth preferred embodiment differs from that according to the first embodiment in that as shown in FIG. 18, the first collimator 10 supported for movement between the inserted and retracted positions with respect to the path of travel of the fluorescent X-rays 5 comprises a generally oblong plate formed with apertures 12a and 12b defined therein in a row in a direction conforming to the direction of movement thereof. Also, the fluorescent X-ray analyzer shown in FIG. 18 further comprises a second collimator 40 supported for movement between inserted and retracted positions with respect to the path of travel of the fluorescent X-rays 5 and positioned between the first collimator 10 and the detecting means 6. This second collimator 40 similarly comprises a generally oblong plate having apertures 42a, 42b and 42c defined therein in a row in a direction conforming to the direction of movement thereof and having a diameter larger than that of the apertures 12a and 12b in the first collimator 10.

According to the eighth embodiment shown in FIG. 18, since the first and second collimators 10 and 40 is of a generally plate-like configuration, they can be easily manufactured. Also, the apertures 12a and 12b of a smaller diameter are positioned closer to the sample piece than the apertures 42a to 42c of a larger diameter, the S/N ratio can be improved particularly where the sample piece 1 is small. Moreover, as compared with the single collimator having all of the apertures, each of the first and second collimators 10 and 40 can have a reduced length and, by moving the first and second collimators 10 and 40, respectively, the stroke of sliding motion of each of the first and second collimators 10 and 40 can be reduced.

Although in the illustrated embodiment each of the first and second collimators 10 and 40 has shown and described as having a plurality of apertures defined therein and having a respective diameter corresponding to the size of the target area of the sample piece to be measured, a single aperture may be sufficient in each of the first and second collimators 10 and 40.

Also, even in any one of the third to eighth embodiments of the present invention, as is the case with any one of the first and second embodiments, there may be employed the drive mechanism 24 for moving the sample piece 1 to the optimum position at which the radiation intensity of the primary X-rays towards the target area of the sample piece 1 can be maximized depending on the size of the target area of the sample piece 1 to be measured, in which case the apertures in each of the first and second collimators 10 and 40 are arranged so as to encompass the target area of the sample piece 1 to be measured, as viewed from the detecting means 6.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A fluorescent X-ray analyzer which comprises:
   a detecting means for detecting fluorescent X-rays emitted from a sample piece to be analyzed; and
   a first collimator disposed between the sample piece and the detecting means and supported for movement between inserted and retracted positions with respect to a path of travel of the fluorescent X-rays towards the detecting means;
   said first collimator comprising a wall adjacent the sample piece that is stepped to provide stepped wall segments having respective apertures of varying diameters defined therein, the smaller the aperture, the closer it being when one of the apertures is selected according to a size of a target area of the sample piece to be measured and is then brought in register with the path of travel of the fluorescent X-rays towards the detecting means.

2. The fluorescent X-ray analyzer as claimed in claim 1, wherein the first collimator comprises a substrate and a projection formed on the substrate, said projection having a tip where the stepped wall segments are formed.

3. The fluorescent X-ray analyzer as claimed in claim 1, further comprising a second collimator disposed between the first collimator and the detecting means and supported for movement between inserted and retracted positions with respect to the path of travel of the fluorescent X-rays towards the detecting means, said second collimator having one or more apertures of a diameter larger than that of any one of the apertures in the first collimator.

4. The fluorescent X-ray analyzer as claimed in claim 1, further comprising a drive mechanism for moving the sample piece to an optimum position at which a radiation intensity of primary X-rays towards a target area of the sample piece to be measured can be maximized depending on the size of the target area of the sample piece, and wherein the apertures in the first collimator are arranged so as to encompass the target area of the sample piece as viewed from the detecting means.

5. A fluorescent X-ray analyzer which comprises:
   an X-ray source for emitting primary X-rays to a sample piece to be analyzed;
   a detecting means for detecting fluorescent X-rays emitted from a sample piece; and
   a first collimator disposed between the sample piece and the detecting means, said first collimator having a plurality of apertures defined therein, and having a flat wall adjacent the sample piece, at least a portion of said flat wall being positioned within an area of irradiation of the primary X-rays, and a shielding wall, disposed downstream of said first wall, for preventing the primary X-rays from entering a path of travel of the fluorescent X-rays from the side of the detecting means of the wall adjacent the sample.

6. The fluorescent X-ray analyzer as claimed in claim 5, further comprising a second collimator supported for movement between inserted and retracted position with respect to the path of travel of the fluorescent X-rays, said second collimator having one or more apertures of a diameter larger than that of any one of the plural aperture in the first collimator.

7. The fluorescent X-ray analyzer as claimed in claim 5, further comprising a drive mechanism for moving the sample piece to an optimum position at which a radiation intensity of a primary X-rays towards a target area of the sample piece to be measured can be maximized depending on the size of the target area of the sample piece, and wherein the apertures in the first collimator are arranged so as to encompass the target area of the sample piece as viewed from the detecting means.

8. A fluorescent X-ray analyzer which comprises:
   an X-ray source for emitting primary X-rays to a sample piece to be analyzed;
   a detecting means for detecting fluorescent X-rays emitted from a sample piece to be analyzed; and
   a first collimator disposed between the sample piece and the detecting means, said first collimator comprising a flat wall adjacent the sample piece and having a plurality of apertures defined therein, and a shielding portion provided at a front side of said flat wall and extending forwardly of the apertures for preventing primary X-rays, generated by the X-ray source, from entering any one of the apertures.

9. The fluorescent X-ray analyzer as claimed in claim 8, further comprising a sample table for supporting the sample piece thereby and wherein said first collimator is arranged so as to receive fluorescent X-rays in a direction inclined relative to the sample table, said first collimator having a corner area confronting the sample table, said corner area being cutout to define a cutout surface parallel to a surface of the sample table.

10. The fluorescent X-ray analyzer as claimed in claim 8, wherein said shielding portion is either a visor formed integrally with the first collimator or a visor formed by fitting a separate plate to the first collimator.

11. The fluorescent X-ray analyzer as claimed in claim 10, wherein the visor of the first collimator has an extension which is formed with a primary X-ray aperture.

12. The fluorescent X-ray analyzer as claimed in claim 8, wherein said shielding portion is arranged to incline in a direction in which a portion of the wall adjacent the sample piece close towards the X-ray source approaches a center axis of the X-ray source.

13. The fluorescent X-ray analyzer as claimed in claim 8, further comprising a second collimator supported for movement between inserted and retracted position with respect to the path of travel of the fluorescent X-rays, said second collimator having one or more apertures of a diameter larger than that of any one of the plural aperture in the first collimator.

14. The fluorescent X-ray analyzer as claimed in claim 8, further comprising a drive mechanism for moving the sample piece to an optimum position at which a radiation intensity of primary X-rays towards a target area of the sample piece to be measured can be maximized depending on the size of the target area of the sample piece, and wherein the apertures in the first collimator are arranged so as to encompass the target area of the sample piece as viewed from the detecting means.

15. A fluorescent X-ray analyzer which comprises:
   a detecting means for detecting fluorescent X-rays emitted from a sample piece to be analyzed; and
   a first collimator comprises a plate member having a plurality of apertures defined therein and supported for movement between inserted and retracted position with respect to a path of travel of fluorescent X-rays; and
   a second collimator disposed between the first collimator and the detecting means and comprising a plate member having apertures defined therein of a diameter larger than that of the apertures in the first collimator, said second collimator being supported for movement between inserted and retracted position with respect to the path of travel of the fluorescent X-rays.

16. The fluorescent X-ray analyzer as claimed in claim 15, further comprising a drive mechanism for moving a sample piece to an optimum position at which a radiation intensity of primary X-rays towards a target area of the sample piece to be measured can be maximized depending on the size of the target area of the sample piece, and wherein the apertures in the first and second collimators are arranged so as to encompass the target area of the sample piece as viewed from the detecting means.

* * * * *